(12) United States Patent
Sack

(10) Patent No.: US 10,405,992 B2
(45) Date of Patent: Sep. 10, 2019

(54) SPINAL FUSION IMPLANT

(71) Applicant: Institute for Musculoskeletal Science and Education, Ltd., Wayne, PA (US)

(72) Inventor: James A. Sack, Elverson, PA (US)

(73) Assignee: Institute for Musculoskeletal Science and Education, Ltd., King of Prussia, PA (US)

( * ) Notice: Subject to any disclaimer, the term of this patent is extended or adjusted under 35 U.S.C. 154(b) by 267 days.

(21) Appl. No.: 15/333,892

(22) Filed: Oct. 25, 2016

(65) Prior Publication Data

US 2018/0110627 A1 Apr. 26, 2018

(51) Int. Cl.
*A61F 2/44* (2006.01)
*A61F 2/46* (2006.01)
*A61F 2/30* (2006.01)

(52) U.S. Cl.
CPC .......... *A61F 2/4611* (2013.01); *A61F 2/4455* (2013.01); *A61F 2/4465* (2013.01); *A61F 2002/3039* (2013.01); *A61F 2002/3093* (2013.01); *A61F 2002/30387* (2013.01); *A61F 2002/30405* (2013.01); *A61F 2002/30492* (2013.01); *A61F 2002/30507* (2013.01); *A61F 2002/30515* (2013.01); *A61F 2002/30579* (2013.01); *A61F 2002/30841* (2013.01); *A61F 2002/30884* (2013.01); *A61F 2002/4475* (2013.01); *A61F 2002/4629* (2013.01)

(58) Field of Classification Search
CPC .......... A61F 2/447; A61F 2/445; A61F 2/446; A61F 2/4465; A61F 2002/30841; A61F 2002/30848; A61F 2002/30845; A61F 2002/30843
See application file for complete search history.

(56) References Cited

U.S. PATENT DOCUMENTS

| | | |
|---|---|---|
| 5,683,394 A | 11/1997 | Rinner |
| 5,702,391 A | 12/1997 | Lin |
| 5,800,547 A | 9/1998 | Schafer et al. |
| 6,102,950 A * | 8/2000 | Vaccaro ............... A61F 2/4611 606/247 |
| 6,113,638 A | 9/2000 | Williams et al. |
| 6,179,873 B1 | 1/2001 | Zientek |
| 6,251,140 B1 | 6/2001 | Marino et al. |
| 6,447,546 B1 | 9/2002 | Bramlet et al. |
| 6,478,823 B1 | 11/2002 | Michelson |
| 6,527,803 B1 * | 3/2003 | Crozet .................. A61F 2/442 606/31 |

(Continued)

OTHER PUBLICATIONS

International Search Report and Written Opinion dated Jan. 12, 2018 for International Patent Application No. PCT/US2017/56973.

(Continued)

*Primary Examiner* — Matthew J Lawson
(74) *Attorney, Agent, or Firm* — Plumsea Law Group, LLC

(57) ABSTRACT

An implant is described for anterior insertion in the spine. The implant includes a body and a cover, which house one or two blades attached to a blade actuating component. Each blade engages a corresponding channel in the blade actuating component. The blade or blades are extended or retracted when the blade actuating component is driven proximally inward or distally outward. Each blade is reinforced by a bridge portion formed along the distal facing side of the blade.

26 Claims, 33 Drawing Sheets

(56) References Cited

U.S. PATENT DOCUMENTS

| | | |
|---|---|---|
| 6,767,367 B1 | 7/2004 | Michelson |
| 6,800,092 B1 | 10/2004 | Williams et al. |
| 7,214,243 B2 | 5/2007 | Taylor |
| 7,217,293 B2 | 5/2007 | Branch, Jr. |
| 7,223,289 B2 | 5/2007 | Trieu et al. |
| 7,569,074 B2 | 8/2009 | Eisermann et al. |
| 7,594,931 B2 | 9/2009 | Louis et al. |
| 7,594,932 B2 | 9/2009 | Aferzon et al. |
| 7,655,046 B2 | 2/2010 | Dryer et al. |
| 7,749,274 B2 | 7/2010 | Razian |
| 7,771,475 B2 | 8/2010 | Michelson |
| 7,879,099 B2 | 2/2011 | Zipnick |
| 7,972,365 B2 | 7/2011 | Michelson |
| 7,998,211 B2 | 8/2011 | Baccelli et al. |
| 8,062,375 B2 | 11/2011 | Glerum et al. |
| 8,070,812 B2 | 12/2011 | Keller |
| 8,070,819 B2 | 12/2011 | Aferzon et al. |
| 8,075,618 B2 | 12/2011 | Trieu et al. |
| 8,080,062 B2 | 12/2011 | Armstrong et al. |
| 8,100,972 B1 | 1/2012 | Bruffey et al. |
| 8,142,508 B1 | 3/2012 | Bruffey et al. |
| 8,147,556 B2 | 4/2012 | Louis et al. |
| 8,216,313 B2 | 7/2012 | Moore |
| 8,221,502 B2 | 7/2012 | Branch, Jr. |
| 8,257,439 B2 | 9/2012 | Zeegers |
| 8,267,997 B2 | 9/2012 | Colleran |
| 8,273,125 B2 | 9/2012 | Baccelli et al. |
| 8,292,958 B1 | 10/2012 | Bruffey et al. |
| 8,328,870 B2 | 12/2012 | Patel et al. |
| 8,343,219 B2 | 1/2013 | Allain et al. |
| 8,366,774 B1 | 2/2013 | Bruffey et al. |
| 8,377,138 B2 | 2/2013 | Reo |
| 8,409,285 B2 | 4/2013 | Keller |
| 8,460,388 B2 | 6/2013 | Kirwan et al. |
| 8,512,409 B1 | 8/2013 | Mertens et al. |
| 8,518,120 B2 | 8/2013 | Glerum et al. |
| 8,523,946 B1 * | 9/2013 | Swann .................... A61F 2/447 623/17.11 |
| 8,556,979 B2 | 10/2013 | Glerum et al. |
| 8,679,183 B2 | 3/2014 | Glerum et al. |
| 8,685,098 B2 | 4/2014 | Glerum et al. |
| 8,709,086 B2 | 4/2014 | Glerum |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,968,405 B2 | 3/2015 | Kirwan et al. |
| 9,039,771 B2 | 5/2015 | Glerum et al. |
| 9,198,774 B2 | 12/2015 | Pisharodi |
| 9,463,091 B2 * | 10/2016 | Brett ...................... A61F 2/442 |
| 2003/0109928 A1 | 6/2003 | Pasquet et al. |
| 2003/0187436 A1 | 10/2003 | Bolger et al. |
| 2004/0254644 A1 | 12/2004 | Taylor |
| 2005/0027362 A1 | 2/2005 | Williams et al. |
| 2005/0033429 A1 | 2/2005 | Kuo |
| 2005/0049590 A1 | 3/2005 | Alleyne et al. |
| 2006/0069436 A1 * | 3/2006 | Sutton .................. A61B 5/0538 623/17.13 |
| 2007/0270961 A1 | 11/2007 | Ferguson |
| 2008/0051901 A1 | 2/2008 | de Villiers et al. |
| 2008/0051902 A1 | 2/2008 | Dwyer |
| 2008/0133017 A1 | 6/2008 | Beyar et al. |
| 2009/0164020 A1 | 6/2009 | Janowski et al. |
| 2009/0265007 A1 | 10/2009 | Colleran |
| 2010/0016974 A1 | 1/2010 | Janowski et al. |
| 2010/0185289 A1 | 7/2010 | Kirwan et al. |
| 2010/0305704 A1 | 12/2010 | Messerli et al. |
| 2011/0015742 A1 | 1/2011 | Hong |
| 2011/0035007 A1 | 2/2011 | Patel et al. |
| 2011/0166655 A1 | 7/2011 | Michelson |
| 2011/0208311 A1 | 8/2011 | Janowski |
| 2011/0230971 A1 | 9/2011 | Donner et al. |
| 2012/0035729 A1 | 2/2012 | Glerum et al. |
| 2012/0078371 A1 | 3/2012 | Gamache et al. |
| 2012/0095559 A1 | 4/2012 | Woods et al. |
| 2012/0116466 A1 | 5/2012 | Dinville et al. |
| 2012/0150300 A1 | 6/2012 | Nihalani |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158148 A1 | 6/2012 | Glerum et al. |
| 2012/0185049 A1 | 7/2012 | Varela |
| 2012/0191196 A1 | 7/2012 | Louis et al. |
| 2012/0330417 A1 | 12/2012 | Zipnick |
| 2013/0110242 A1 | 5/2013 | Kirwan et al. |
| 2013/0150968 A1 | 6/2013 | Dinville et al. |
| 2013/0166029 A1 | 6/2013 | Dinville et al. |
| 2013/0310935 A1 | 11/2013 | Swann |
| 2013/0338776 A1 | 12/2013 | Jones |
| 2014/0074241 A1 * | 3/2014 | McConnell ........... A61F 2/4455 623/17.16 |
| 2014/0088711 A1 * | 3/2014 | Chin .................. A61F 2/30749 623/17.16 |
| 2014/0114420 A1 | 4/2014 | Robinson |
| 2014/0148904 A1 | 5/2014 | Robinson |
| 2014/0236297 A1 | 8/2014 | Iott et al. |
| 2014/0303731 A1 | 10/2014 | Glerum |
| 2014/0324171 A1 | 10/2014 | Glerum et al. |
| 2014/0379085 A1 | 12/2014 | Duffield et al. |
| 2015/0012097 A1 | 1/2015 | Ibarra et al. |
| 2015/0127107 A1 | 5/2015 | Kim et al. |
| 2015/0202051 A1 * | 7/2015 | Tanaka ................... A61F 2/447 623/17.16 |
| 2015/0250603 A9 | 9/2015 | Glerum et al. |
| 2015/0305880 A1 * | 10/2015 | Kim ..................... A61F 2/4611 623/17.16 |
| 2015/0342754 A1 | 12/2015 | Geebelen et al. |
| 2016/0038845 A1 * | 2/2016 | Mizunaga ........... A63H 17/262 446/431 |
| 2016/0338845 A1 | 11/2016 | Ashleigh |
| 2016/0374831 A1 | 12/2016 | Duffield et al. |
| 2017/0165082 A1 * | 6/2017 | Faulhaber ............... A61F 2/447 |
| 2017/0266016 A1 | 9/2017 | Faulhaber |

OTHER PUBLICATIONS

International Search Report and Written Opinion dated Jan. 23, 2018 for International Patent Application No. PCT/US2017/058109.

* cited by examiner

SPINAL FUSION IMPLANT

BACKGROUND

The embodiments are generally directed to implants for supporting bone growth in a patient.

A variety of different implants are used in the body. Implants used in the body to stabilize an area and promote bone ingrowth provide both stability (i.e. minimal deformation under pressure over time) and space for bone ingrowth.

Spinal fusion, also known as spondylodesis or spondylosyndesis, is a surgical treatment method used for the treatment of various morbidities such as degenerative disc disease, spondylolisthesis (slippage of a vertebra), spinal stenosis, scoliosis, fracture, infection or tumor. The aim of the spinal fusion procedure is to reduce instability and thus pain.

In preparation for the spinal fusion, most of the intervertebral disc is removed. An implant, the spinal fusion cage, may be placed between the vertebra to maintain spine alignment and disc height. The fusion (i.e. bone bridge) occurs between the endplates of the vertebrae.

SUMMARY

In one aspect, an implant includes a housing, where the housing has a first axis, a blade, the blade having a retracted position in the housing and an extended position where the blade extends outwardly from the housing, and a blade actuating component, where the blade actuating component includes a driven shaft portion and a blade engaging portion. The blade actuating component can move the blade between the retracted position and the extended position. In addition, the housing includes a first end, where the first end includes a guide opening, and the guide opening has a hollow grooved portion and a chamber portion. The hollow grooved portion is connected to the chamber portion, and the chamber portion receives a portion of the driven shaft portion of the blade actuating component.

In another aspect, an implant includes a body having a first axis, and a blade having a retracted position in the body and an extended position where the blade extends outwardly from the body. The blade has a distal face and a proximal face. In addition, the blade has a bridge portion disposed adjacent to the distal face, where the bridge portion is configured to provide structural reinforcement to the blade. The implant further includes a blade actuating component that can translate through the body in directions parallel to the first axis, and the blade actuating component can move the blade between the retracted position and the extended position.

In another aspect, an implant includes a housing, a first blade, and a blade actuating component. The first blade has a retracted position in the housing and an extended position where the first blade extends outwardly from the housing. In addition, the blade actuating component is configured to translate through the housing in directions parallel to a first axis, where the first axis extends from an anterior side of the implant to a posterior side of the implant. The blade actuating component comprises a driven shaft portion and a blade engaging portion, the driven shaft portion being disposed at least partially outside of the housing when the first blade is the retracted position, and the driven shaft portion being disposed entirely within the housing when the first blade is in the extended position.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, with emphasis instead being placed upon illustrating the principles of the embodiments. Moreover, in the figures, like reference numerals designate corresponding parts throughout the different views.

DETAILED DESCRIPTION

The embodiments described herein are directed to an implant for use in a spine. The embodiments include implants with a body and one or more blades. In addition to the various provisions discussed below, any embodiments may make use of any of the body/support structures, blades, actuating components or other structures disclosed in Duffield et al., U.S. Pat. No. 9,707,100, issued on Jul. 18, 2017, and titled "Interbody Fusion Device and System for Implantation," Sack, U.S. Pat. No. 10,307,265, issued on Jun. 4, 2019, and titled "Implant With Deployable Blades," and Duffield et al., U.S. Patent Publication Number 2017/0100260, published on Apr. 13, 2017, and titled "Insertion Tool For Implant And Methods of Use," each of which are hereby incorporated by reference in their entirety.

Introduction to the Implant

Figure 1:
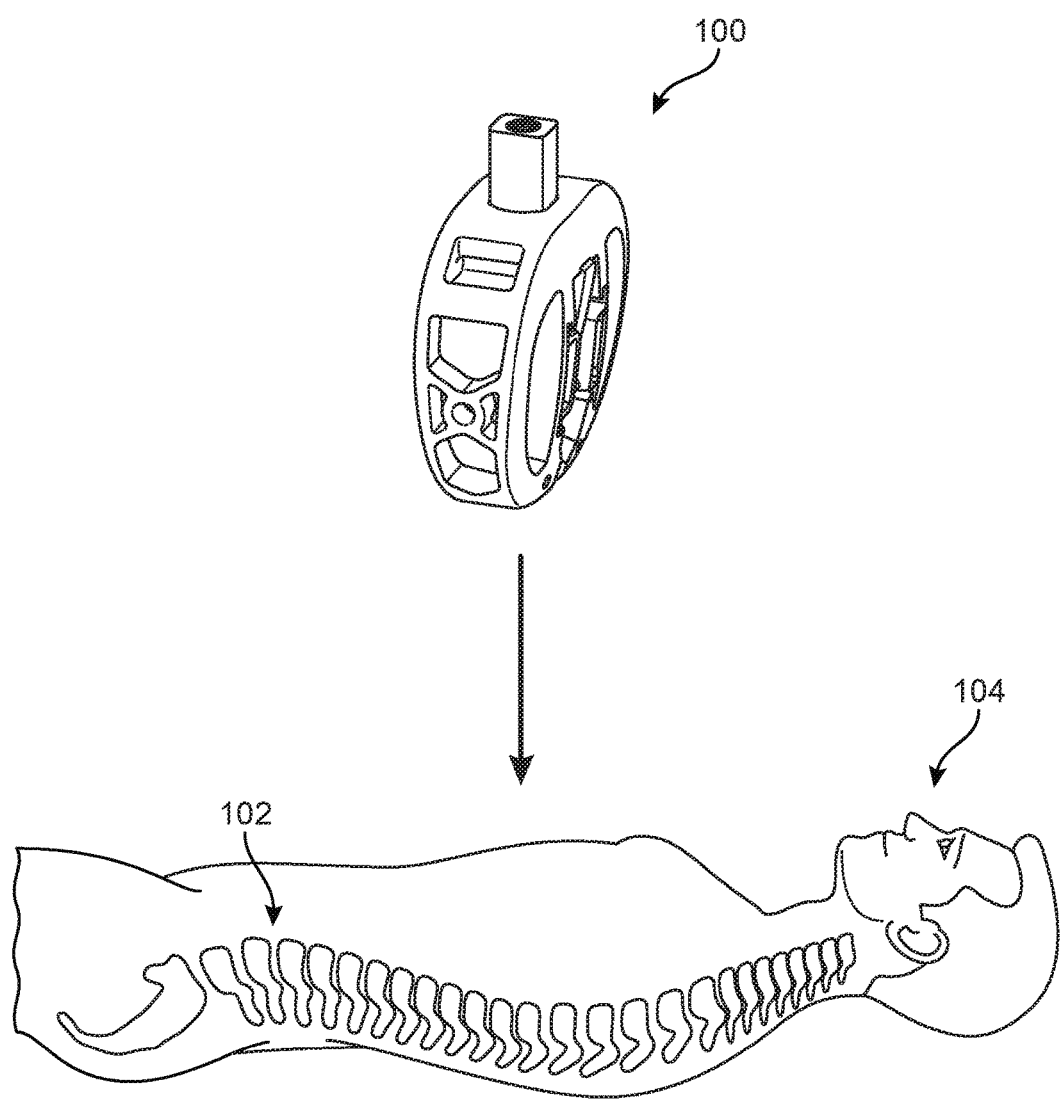
FIG. 1 is a schematic view of a patient and an implant, according to an embodiment.
Figure 2:
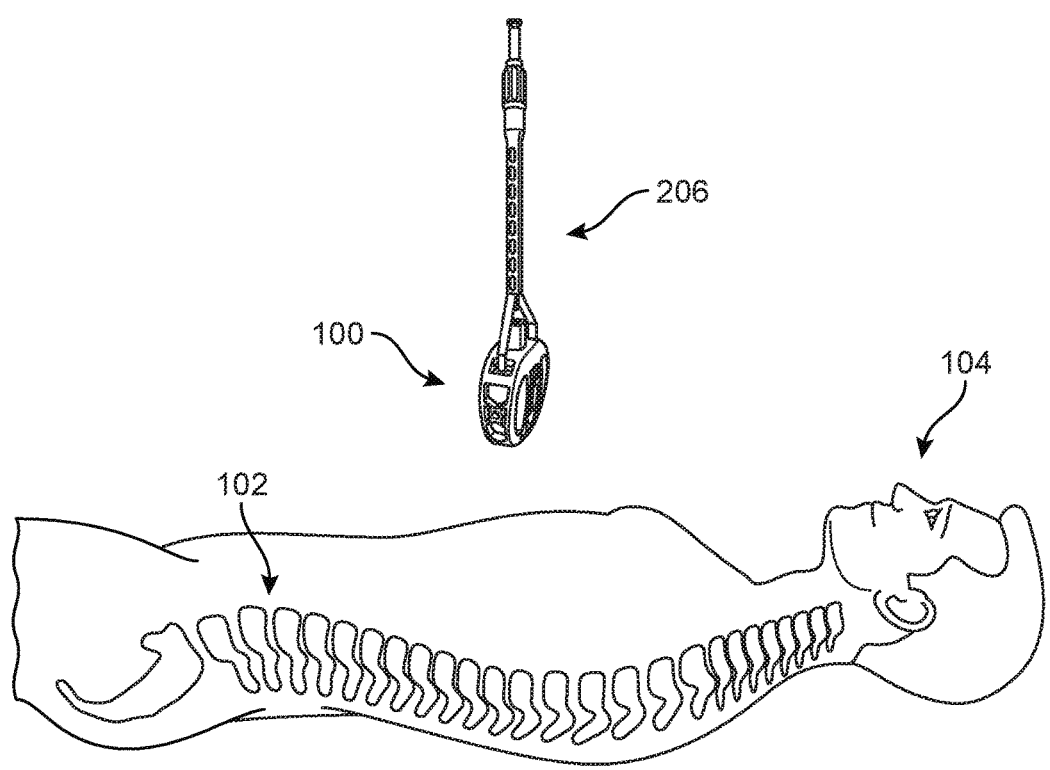
FIG. 2 is a schematic view of a patient and an implant with an insertion tool, according to an embodiment.
Figure 3:
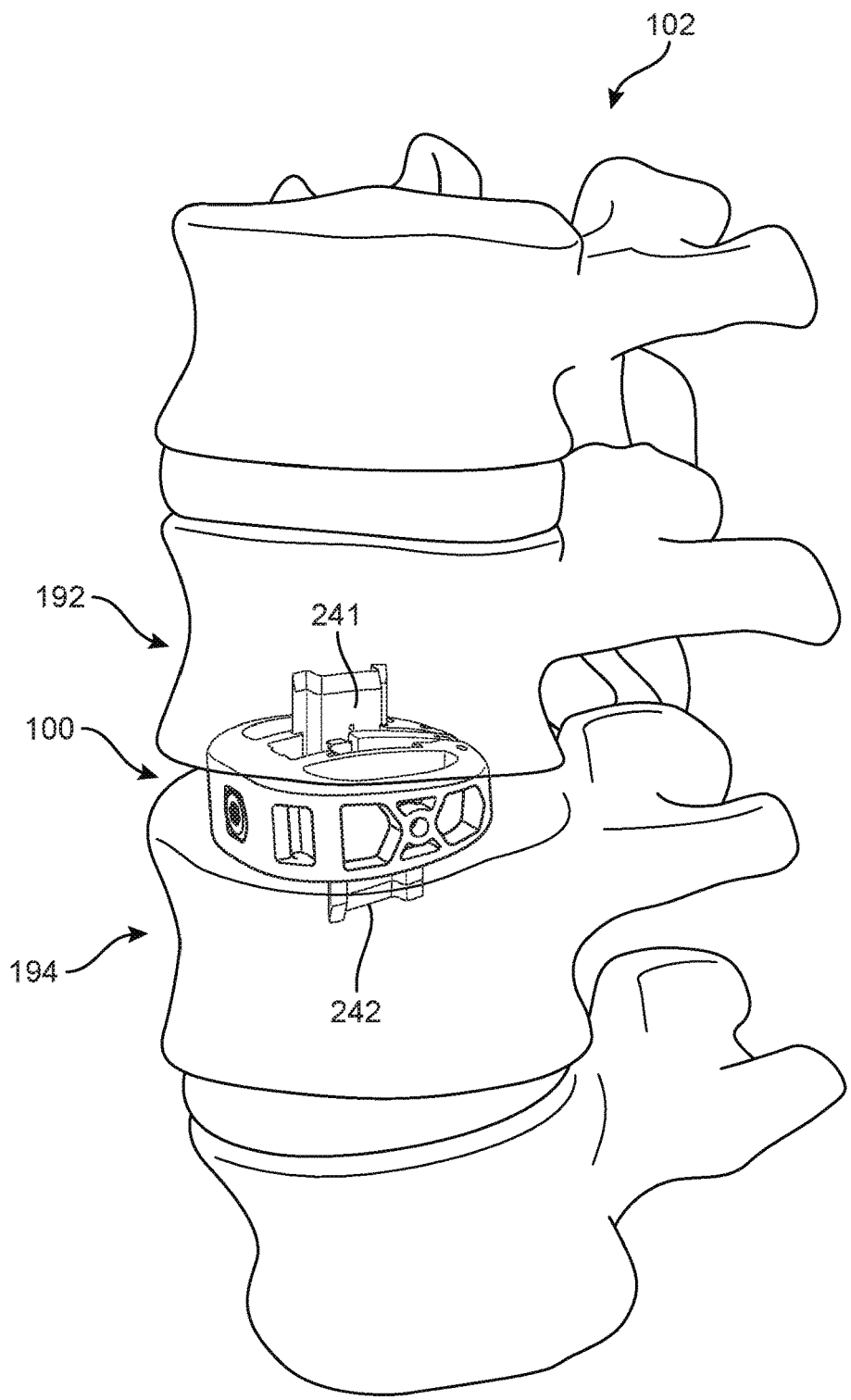
FIG. 3 is a schematic view of a spine and a deployed implant, according to an embodiment.

FIG. 1 is a schematic view of an embodiment of an implant 100. For purposes of context, implant 100 is shown adjacent to a depiction of a spinal column 102 in a human body 104. In FIG. 2, an embodiment of implant 100 is shown as it is being inserted into human body 104 with the use of an insertion tool 206. It should be understood that the relative size of implant 100 and insertion tool 206 as depicted with human body 104 have been adjusted for purposes of illustration. For purposes of this disclosure, implant 100 may also be referred to as a cage or fusion device. In some embodiments, implant 100 is configured to be implanted within a portion of the human body. In some embodiments, implant 100 may be configured for implantation into the spine. In some embodiments, implant 100 may be a spinal fusion implant, or spinal fusion device, which is inserted between adjacent vertebrae to provide support and/or facilitate fusion between the vertebrae. For example, referring to FIG. 3, a section of spinal column 102 is illustrated, where implant 100 has been positioned between a first vertebra 192 and a second vertebra 194. Moreover, implant 100 is seen to include two blades (a first blade 241 and a second blade 242), which extend from the superior and inferior surfaces of implant 100. Each of the blades has been driven into an adjacent vertebra (i.e., first vertebra 192 or second vertebra 194) so as to help anchor implant 100.

In some embodiments, implant 100 may be inserted using an anterior lumbar interbody fusion (ALIF) surgical procedure, where the disc space is fused by approaching the spine through the abdomen. In the ALIF approach, a three-inch to five-inch incision is typically made near the abdomen and the abdominal muscles are retracted to the side. In some cases, implant 100 can be inserted through a small incision in the front or anterior side of the body. In some cases, an anterior approach may afford improved exposure to the disc space to a surgeon. The anterior approach can allow a larger device to be used for the fusion, increasing the surface area for a fusion to occur and allowing for more postoperative stability. An anterior approach often makes it possible to reduce some of the deformity caused by various conditions, such as isthmic spondylolisthesis. Insertion and placement of the disc along the front of a human body can also re-establish the patient's normal sagittal alignment in some cases, giving individuals a more normal inward curve to their low back.

For purposes of clarity, reference is made to various directional adjectives throughout the detailed description and in the claims. As used herein, the term "anterior" refers to a side or portion of an implant that is intended to be oriented towards the front of the human body when the implant has been placed in the body. Likewise, the term "posterior" refers to a side or portion of an implant that is intended to be oriented towards the back of the human body following implantation. In addition, the term "superior" refers to a side or portion of an implant that is intended to be oriented towards a top (e.g., the head) of the body while "inferior" refers to a side or portion of an implant that is intended to be oriented towards a bottom of the body. Reference is also made herein to "lateral" sides or portions of an implant, which are sides or portions facing along a lateral direction of the body.

Figure 4:
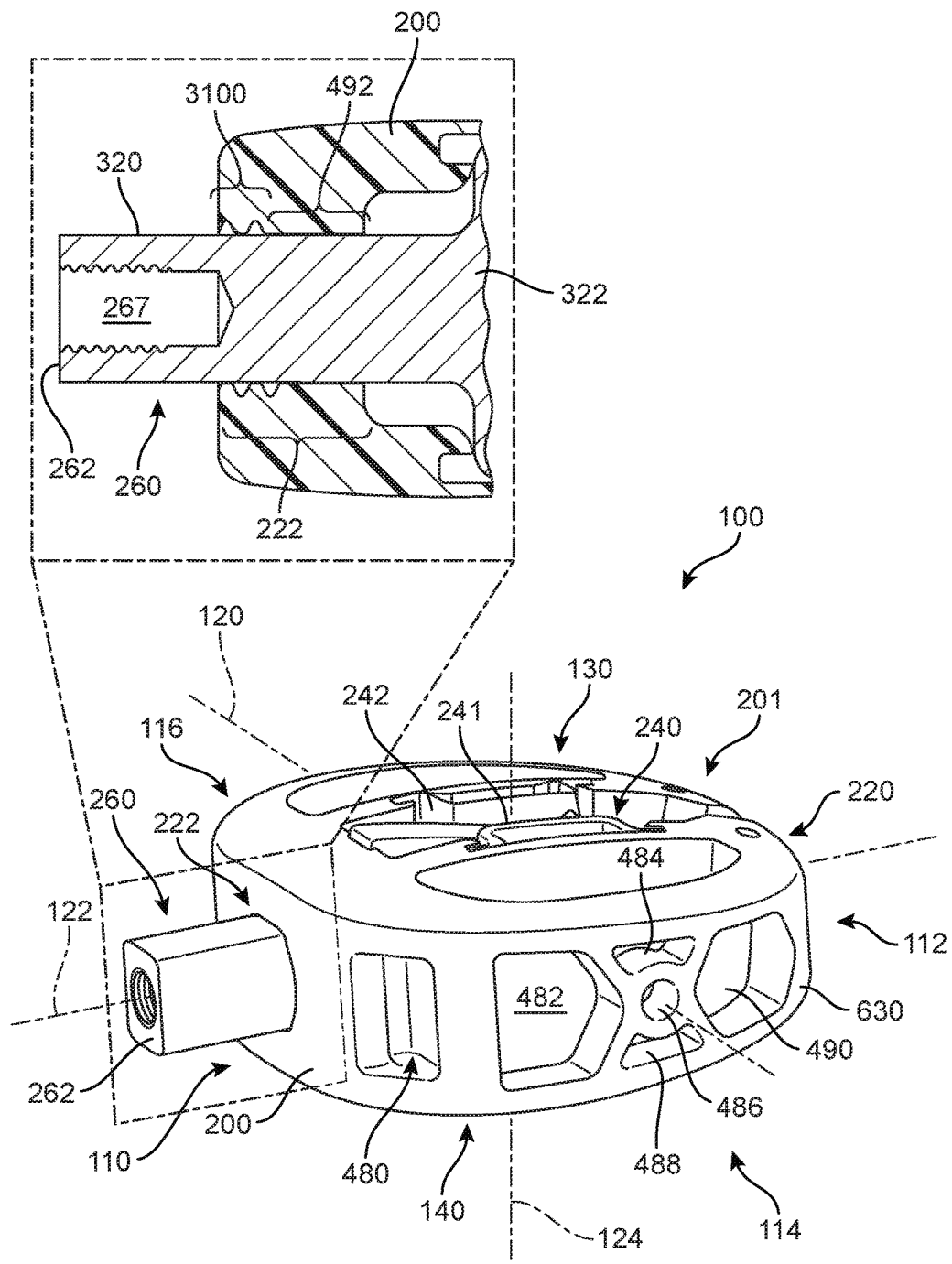
FIG. 4 is an isometric view of an embodiment of an implant.

FIG. 4 is a schematic isometric view of an embodiment of implant 100, according to an embodiment. As seen in FIG. 4, implant 100 is understood to be configured with an anterior side 110 and a posterior side 112. Implant 100 may also include a first lateral side 114 and a second lateral side 116. Furthermore, implant 100 may also include a superior side 130 and an inferior side 140.

Reference is also made to directions or axes that are relative to the implant itself, rather than to its intended orientation with regards to the body. For example, the term "distal" refers to a part that is located further from a center of an implant, while the term "proximal" refers to a part that is located closer to the center of the implant. As used herein, the "center of the implant" could be the center of mass and/or a central plane and/or another centrally located reference surface.

An implant may also be associated with various axes. Referring to FIG. 4, implant 100 may be associated with a longitudinal axis 120 that extends along the longest dimension of implant 100 between first lateral side 114 and second lateral side 116. Additionally, implant 100 may be associated with a posterior-anterior axis 122 (also referred to as a "widthwise axis") that extends along the widthwise dimension of implant 100, between posterior side 112 and anterior side 110. Moreover, implant 100 may be associated with a vertical axis 124 that extends along the thickness dimension of implant 100 and which is generally perpendicular to both longitudinal axis 120 and posterior-anterior axis 122.

An implant may also be associated with various reference planes or surfaces. As used herein, the term "median plane" refers to a vertical plane which passes from the anterior side to the posterior side of the implant, dividing the implant into right and left halves, or lateral halves. As used herein, the term "transverse plane" refers to a horizontal plane located in the center of the implant that divides the implant into superior and inferior halves. As used herein, the term "coronal plane" refers to a vertical plane located in the center of the implant that divides the implant into anterior and posterior halves. In some embodiments, the implant is symmetric or substantially symmetric about two planes, such as the median and the transverse plane.

Figure 5:
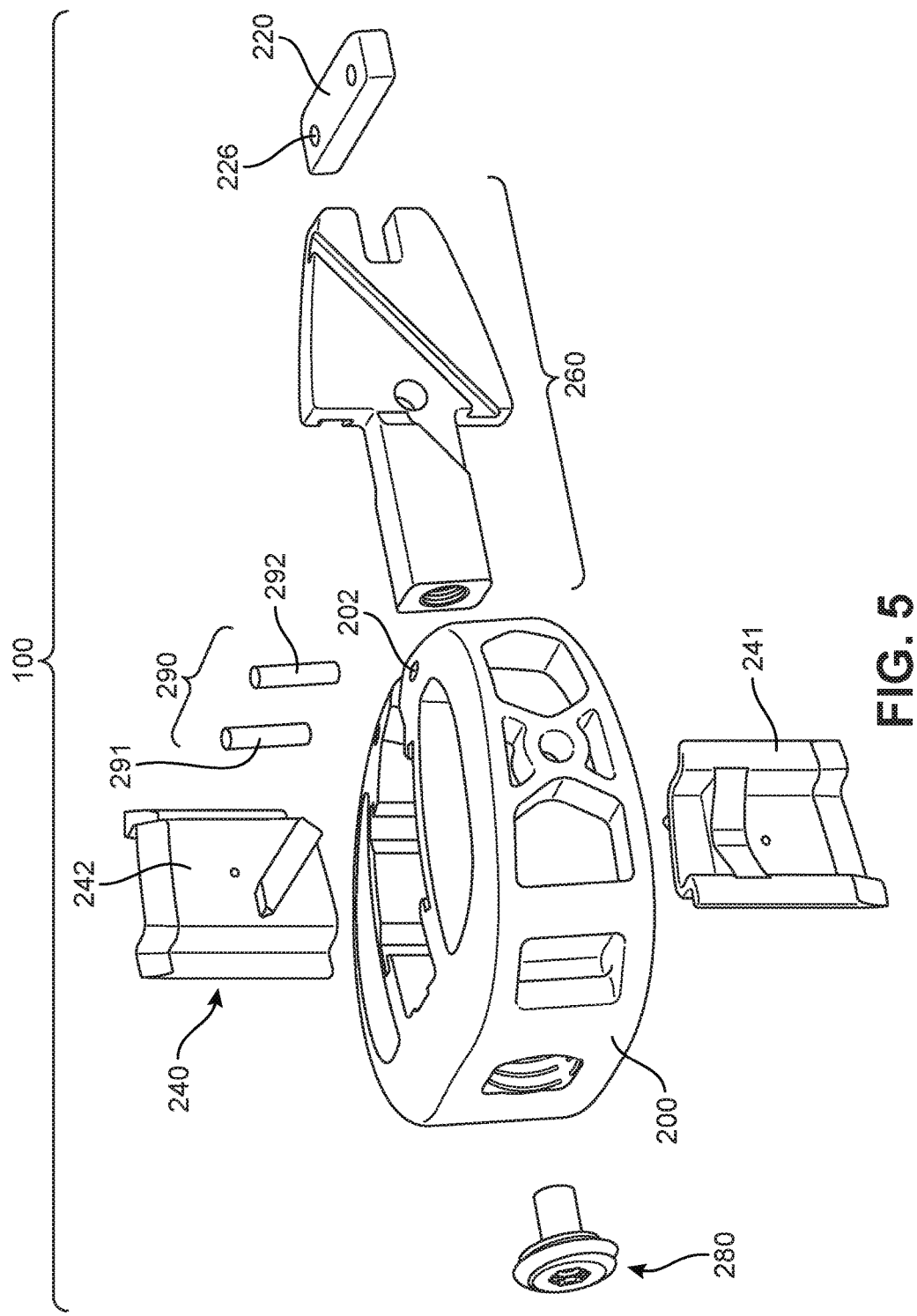
FIG. 5 is an exploded isometric view of the implant of FIG. 4.

FIG. 5 is a schematic isometric exploded view of implant 100 according to an embodiment. Referring to FIGS. 4-5, implant 100 is comprised of a body 200 and a cover 220, which together may be referred to as a housing 201 of implant 100. In some embodiments, a body and cover may be integrally formed. In other embodiments, a body and cover may be separate pieces that are joined by one or more fasteners. In the embodiment of FIGS. 4-5, body 200 and cover 220 are separate pieces that are fastened together using additional components of implant 100.

Embodiments of an implant may include provisions for anchoring the implant into adjacent vertebral bodies. In some embodiments, an implant may include one or more anchoring members. In the embodiment of FIGS. 4-5, implant 100 includes a set of blades 240 that facilitate anchoring implant 100 to adjacent vertebral bodies following insertion of implant 100 between the vertebral bodies. Set of blades 240 may be further comprised of first blade 241 and second blade 242. Although the exemplary embodiments described herein include two blades, other embodiments of an implant could include any other number of blades. For example, in another embodiment, three blades could be used. In another embodiment, four blades could be used, with two blades extending from the inferior surface and two blades extending from the superior surface of the implant. Still other embodiments could include five or more blades. In yet another embodiment, a single blade could be used.

An implant with blades can include provisions for moving the blades with respect to a housing of the implant. In some embodiments, an implant includes a blade actuating component that engages with one or more blades to extend and/or retract the blades from the surfaces of the implant. In the embodiment shown in FIGS. 4-5, implant 100 includes a blade actuating component 260. In some embodiments, blade actuating component 260 is coupled to first blade 241 and second blade 242. Moreover, by adjusting the position of blade actuating component 260 within housing 201, first blade 241 and second blade 242 can be retracted into, or extended from, surfaces of implant 100.

An implant can include provisions for locking the position of one or more elements of the implant. In embodiments where the position of a blade actuating component can be changed, an implant can include provisions for locking the actuating component in a given position, thereby also locking one or more blades in a given position, such as through the use of a threaded fastener or other type of securing mechanism. In the embodiment shown in FIG. 5, implant 100 includes locking screw 280. In some embodiments, locking screw 280 can be used to lock blade actuating component 260 in place within implant 100, which ensures first blade 241 and second blade 242 remain in an extended or deployed position, as will be shown further below.

Embodiments can also include one or more fasteners that help attach a body to a cover. In some embodiments, pins, screws, nails, bolts, clips, or any other kinds of fasteners could be used. In the embodiment shown in FIG. 5, implant 100 includes a set of pins 290 that help fasten cover 220 to body 200. In the exemplary embodiments, two pins are used, including first pin 291 and second pin 292. In other embodiments, however, any other number of pins could be used. In another embodiment, a single pin could be used. In still other embodiments, three or more pins could be used.

Body Component

Figure 6:
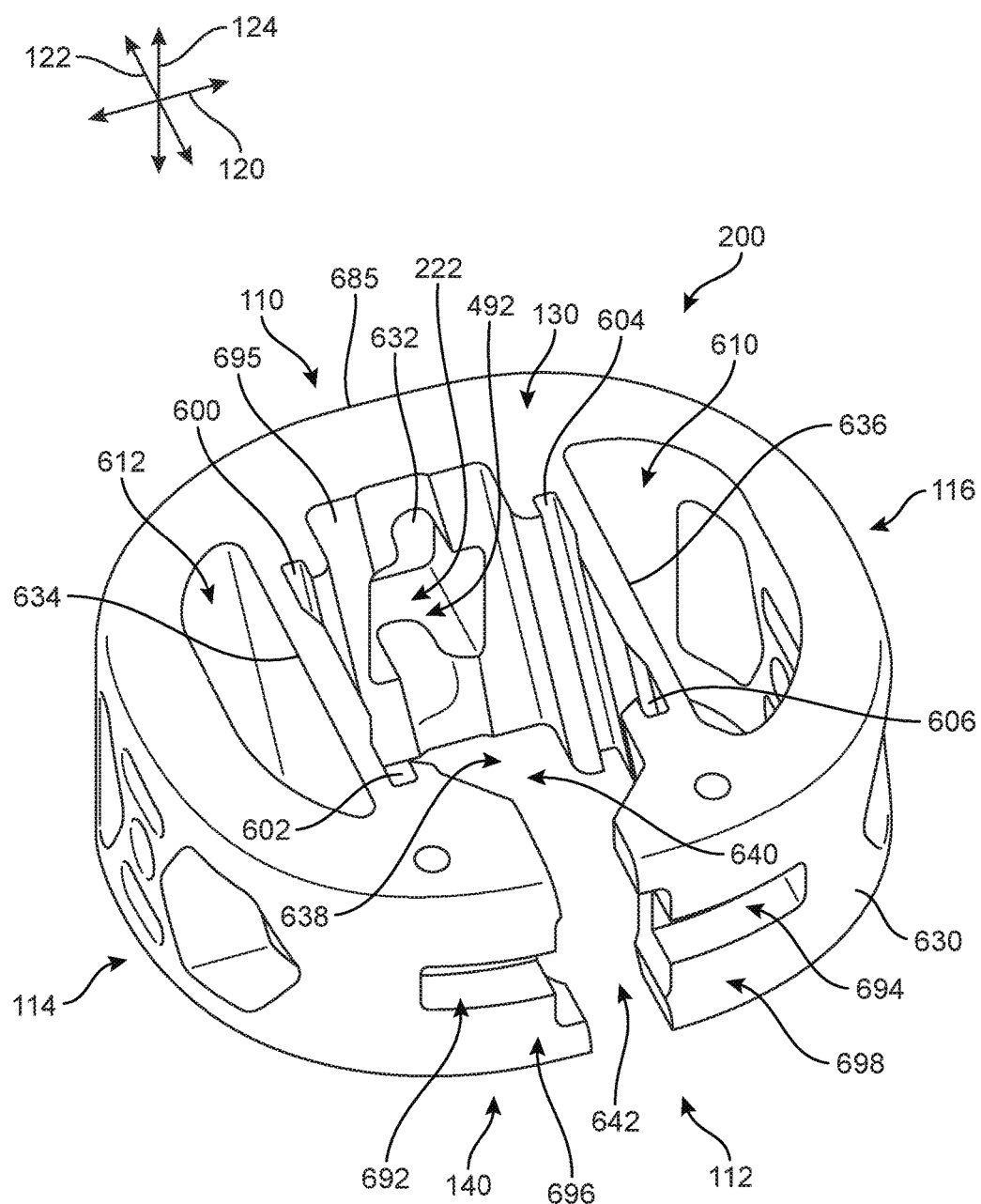
FIG. 6 is an isometric superior view of an embodiment of a body of an implant.
Figure 7:
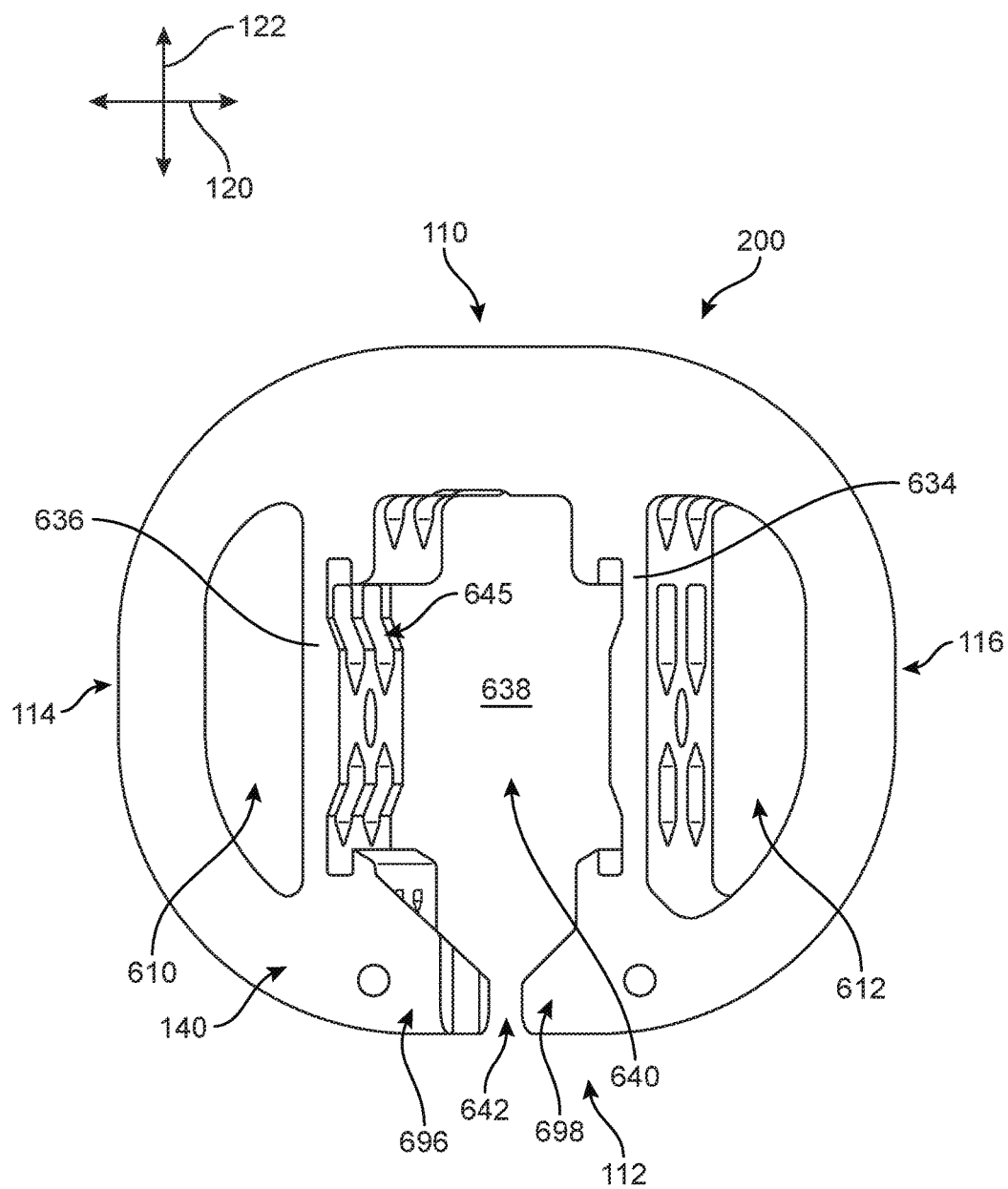
FIG. 7 is an isometric inferior view of an embodiment of a body of an implant.
Figure 8:
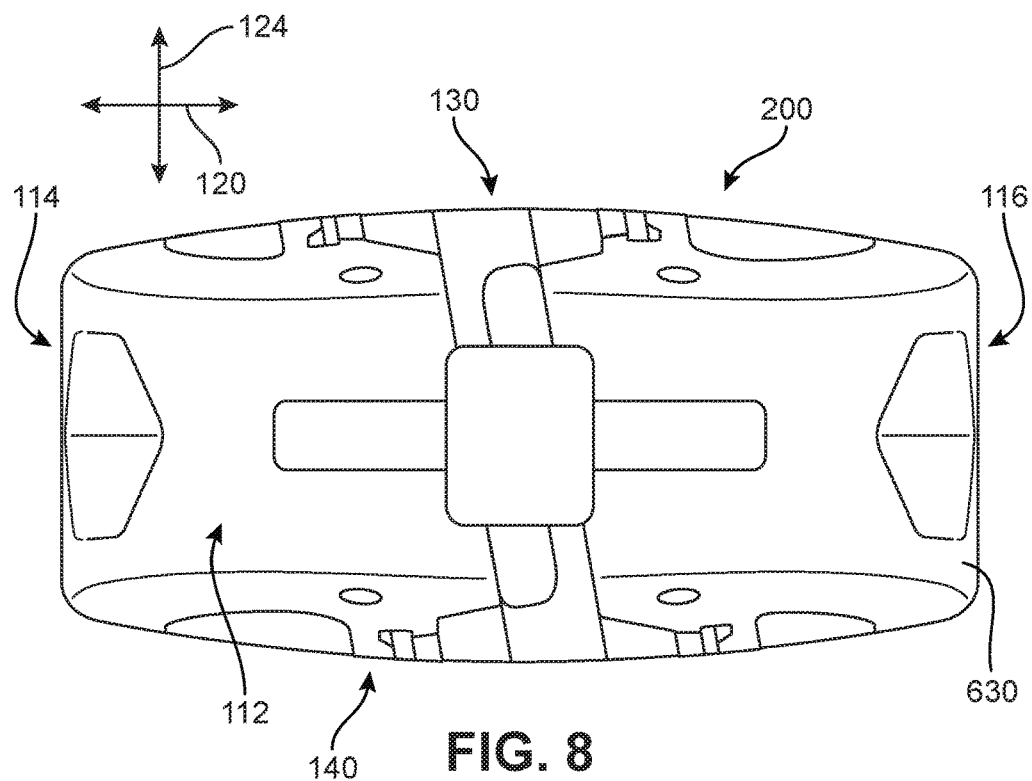
FIG. 8 is a schematic posterior-side view of an embodiment of a body of an implant.
Figure 9:
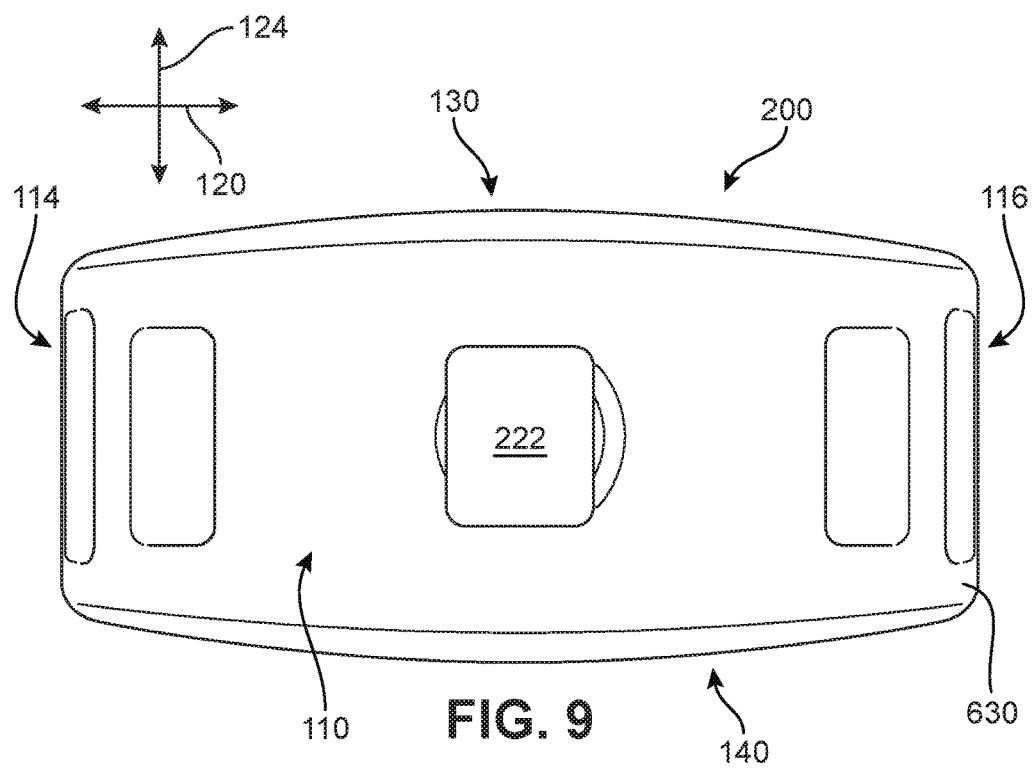
FIG. 9 is a schematic anterior-side view of an embodiment of a body of an implant.

Referring now to FIGS. 6-9, four views are presented of an embodiment of body 200. FIG. 6 is a schematic isometric superior side or top-down isometric view of body 200. FIG. 7 depicts a schematic isometric inferior side or bottom-up isometric view of body 200. FIG. 8 is a schematic posterior or rear side view of body 200. FIG. 9 is a schematic anterior or front side view of body 200. In different embodiments, body 200 may provide the posterior and anterior sides of housing 201, as well as at least one lateral side of housing 201.

In some embodiments, the lateral sides of a body may both have a lattice-like geometry. Various openings or apertures, as will be discussed below, can help reduce the overall weight of the implant, and/or decrease manufacturing costs associated with material usage. Furthermore, in some cases, openings can increase the surface area available throughout body 200, and facilitate the application of bone growth promoting materials to the implant, and/or facilitate the coupling of the implant with the insertion tool, as will be discussed further below. In some other embodiments, the lateral sides could be configured as solid walls with one or more openings. Furthermore, by providing openings in the housing of the implant, there can be improved visual clarity regarding the degree or extent of blade deployment.

In the exemplary embodiment shown in FIGS. 6-9, body 200 has a generally oval cross-sectional shape in a horizontal plane. Furthermore, each of superior side 130 and inferior side 140 include at least one through-hole opening. For example, in FIGS. 6 and 7, it can be seen that implant 100 includes a first opening 610 and a second opening 612. Each of first opening 610 and second opening 612 extend continuously through the thickness of implant 100 from superior side 130 to inferior side 140 in a direction substantially aligned with vertical axis 124. While the openings can vary in size, shape, and dimension in different embodiments, in one embodiment both first opening 610 and second opening 612 each have a generally half-circle or semi-circle cross-sectional shape along the horizontal plane.

In addition, as shown in FIGS. 8 and 9, posterior side 112 and anterior side 110 of body 200 have a generally oblong rectangular shape. Furthermore, in FIGS. 4, 6 and 8-9, it can be seen that a sidewall 630 extends around the majority of perimeter of body 200, extending between superior side 130 to inferior side 140 in a direction substantially aligned with vertical axis 124, forming a periphery that surrounds or defines a majority of the outer surface of the implant. In some embodiments, first lateral side 114 and second lateral side 116 are substantially similar (i.e., can include substantially similar structural features), though in other embodiments, each side can include variations. There may be additional openings formed in implant 100 in some embodiments. In different embodiments, sidewall 630 can include a plurality of side openings or apertures, though in other embodiments, sidewall 630 can be substantially continuous or solid.

Referring back to FIG. 4, it can be seen that first lateral side 114 includes a first aperture 480, a second aperture 482, a third aperture 484, a fourth aperture 486, a fifth aperture 488, and a sixth aperture 490. Each aperture can differ in shape in some embodiments. For example, first aperture 480 has a substantially oblong rectangular shape, second aperture 482 has a five-sided or substantially pentagonal shape, third aperture 484 and fifth aperture 488 each have a four-sided or substantially trapezoidal shape, fourth aperture 486 has a substantially round shape, and sixth aperture 490 has a six-sided or substantially hexagonal shape. In other embodiments, second lateral side 116 can include a fewer or greater number of apertures. It should be understood that second lateral side 116 can also include a plurality of apertures disposed in a similar arrangement as first lateral side 114 in some embodiments. The shapes of the various openings are configured to permit the implant body to be manufactured in the Direct Metal Laser Sintering (DMLS) process, as well as to provide support to the inferior and superior load bearing surfaces.

Figure 31:
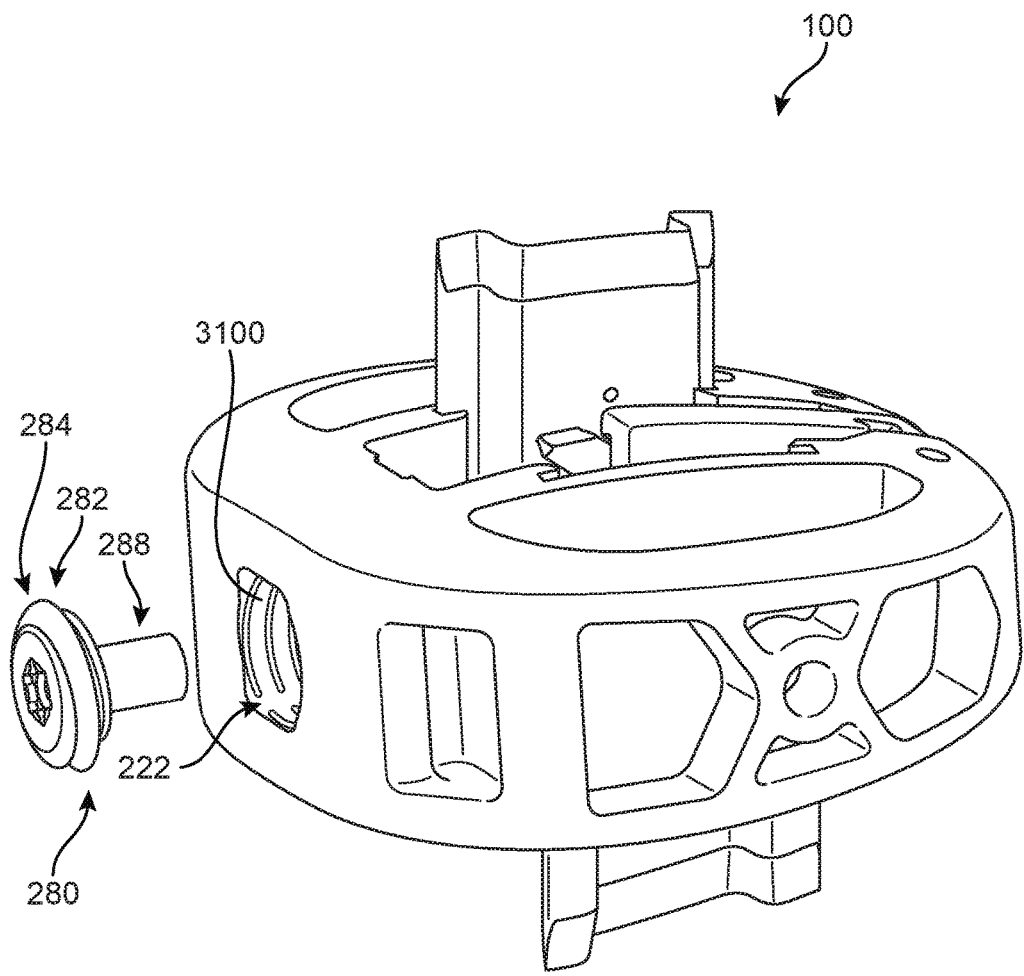
FIG. 31 is a schematic isometric view of an implant with a locking screw, according to an embodiment.
Figure 32:
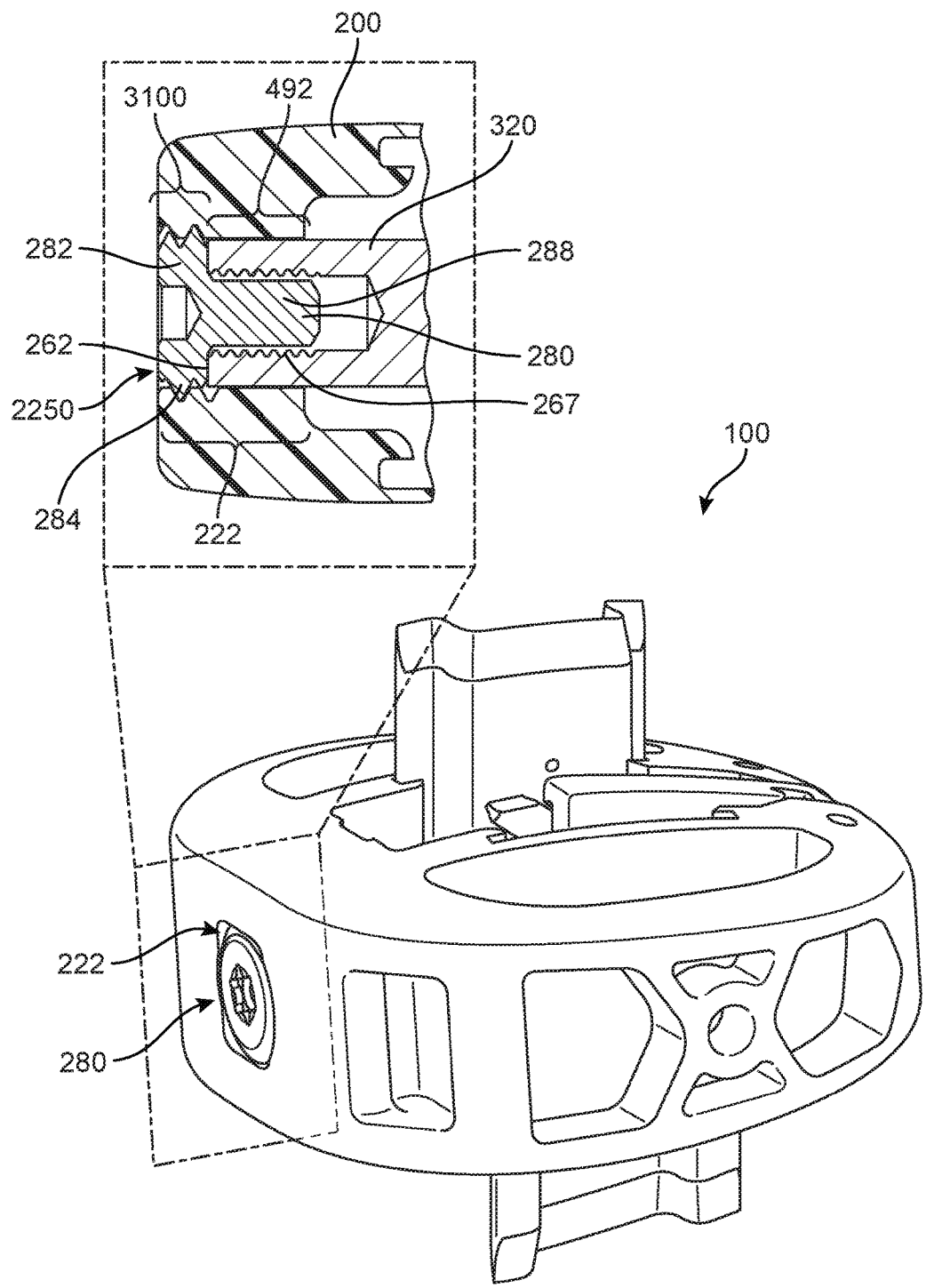
FIG. 32 is a schematic isometric view of an implant with a locking screw, according to an embodiment.

As shown in FIG. 6, in one embodiment, anterior side 110 of body 200 includes guide opening 222. Guide opening 222 extends through the thickness of sidewall 630 in a direction substantially aligned with posterior-anterior axis 122. Guide opening 222 includes a chamber portion ("chamber") 492 and a hollow grooved portion (the hollow grooved portion will be discussed further below with respect to FIGS. 31 and 32). Chamber 492 can be understood to be connected with the grooved portion such that some components can pass from chamber 492 into the grooved portion (or vice versa).

In some embodiments, as will be discussed further below and is shown generally in FIG. 4, a portion of blade actuating component 260 can be configured to extend through or be received by the chamber portion. In other words, in some embodiments, the chamber portion can be sized and dimensioned to fit or extend closely around a portion of blade actuating component 260. In FIG. 6, it can be seen that chamber 492 comprises a generally oblong four-sided opening. In one embodiment, chamber 492 has a substantially oblong square or rectangular cross-sectional shape in a vertical plane. In FIG. 6, chamber 492 extends between an outwardly-facing or distally oriented surface 685 of sidewall 630 and an inwardly-facing or proximally oriented surface 695 of sidewall 630. As chamber 492 approaches proximally oriented surface 695, there may be additional recessed regions or diagonal slots 632 which expand the size of guide opening 222, and can be configured to snugly receive or fit various portions of blade actuating component 260, as will be discussed further below. Furthermore, it can be understood that the cross-sectional shape of the chamber portion is configured to prevent rotation of the driven shaft portion when the drive shaft portion is inserted into the chamber portion.

Body 200 can also include additional reinforcement structures. For example, as shown in FIGS. 6 and 7, body 200 includes a first inner sidewall 634 extending in a direction substantially aligned with posterior-anterior axis 122 and a second inner sidewall 636 extending in a direction substantially aligned with posterior-anterior axis 122. First inner sidewall 634 and second inner sidewall 636 can be substantially parallel in one embodiment. As noted above, different portions of body 200 can include recessed areas or apertures. In one embodiment, shown best in FIG. 7, first inner sidewall 634 and/or second inner sidewall 636 include a plurality of apertures 645.

Furthermore, in some embodiments, first inner sidewall 634 and second inner sidewall 636 can help define or bound a central hollow region 638 in body 200. Central hollow region 638 can extend through the thickness of body 200. Central hollow region 638 can be configured to receive the blades and the blade actuating component, as will be discussed further below. In FIGS. 6 and 7, it can be seen that central hollow region 638 includes a main opening 640 and a posterior opening 642, where main opening 640 is connected with a posterior opening 642 such that some components can pass from main opening 640 into posterior opening 642. Main opening 640 is located toward a center or middle portion of the body, and posterior opening 642 is located along the posterior periphery of the body. In one embodiment, posterior opening 642 is significantly narrower in width across the horizontal plane relative to the width associated with main opening 640.

In different embodiments, posterior opening 642 can be disposed between a first end portion 696 and a second end portion 698 that are associated with posterior side 112 of body 200. Furthermore, in some embodiments, each end portion can include a recessed region. In FIG. 6, a first posterior recess 692 is formed within a portion of first end portion 696 and a second posterior recess 694 is formed within a portion of second end portion 698. As will be discussed below with respect to FIGS. 20 and 21, first posterior recess 692 and second posterior recess 694 can be configured to receive a cover.

First end portion 696 and a second end portion 698 can be substantially similar in some embodiments. In one embodiment, first end portion 696 and a second end portion 698 are mirror-images of one another relative to a central posterior-anterior axis or midline. In some embodiments, first posterior recess 692 and second posterior recess 694 are sized and dimensioned to snugly receive a rearward cover or cap that extends between or bridges together first end portion 696 and second end portion 698 of body 200, providing a substantially continuous outer periphery of the implant. In addition, in some embodiments, either or both of first end portion 696 and second end portion 698 can include pin holes (shown in FIG. 5 as pin holes 202), which can be used to help secure the cover to the posterior side of body 200 (see FIGS. 20-21).

The configuration of body 200 shown for the embodiment of FIGS. 6-9 may facilitate the manufacturing process in different embodiments. In particular, this configuration may permit 3D Printing via laser or electron beam with minimal support structures by forming a unitary piece with a plurality of openings. This design may also help to improve visibility of adjacent bony anatomy under X-ray fluoroscopy while still providing sufficient structural support and rigidity to withstand all testing requirements and the clinical loading of an implant. Other embodiments, not pictured in the figures, include round or rectangular openings in otherwise solid geometry of the anterior, posterior, or lateral sides.

Embodiments can also include one or more blade retaining portions. A blade retaining portion may receive any part of a blade, including one or more edges and/or faces of the blade. In one embodiment, a body includes blade retaining portions to receive the anterior and posterior edges of each blade. As seen in FIG. 6, body 200 includes a first blade retaining portion 600 positioned toward anterior side 110 of first inner sidewall 634 and a second blade retaining portion 602 positioned toward posterior side 112 of first inner sidewall 634. Thus, each blade retaining portion is formed in an outer perimeter of a lateral side of main opening 640 of central hollow region 638. First blade retaining portion 600 comprises a first blade retaining channel extending through the depth of body 200 that is configured to receive an anterior edge of the first blade (see FIG. 13). Likewise, second blade retaining portion 602 comprises a second blade retaining channel extending through the depth of body 200 that is configured to receive a posterior edge of the first blade (see FIG. 13).

In some embodiments, one or more channels can be oriented in a direction that is substantially diagonal relative to the horizontal plane. In one embodiment, a channel can be oriented approximately 45 degrees relative to the horizontal plane. In other embodiments, a channel can be oriented vertically (approximately 90 degrees relative to the horizontal plane) or can be oriented between 30 degrees and 90 degrees relative to the horizontal plane. The orientation of a channel can be configured to correspond to the orientation of the anterior edges and/or posterior edges of a blade in some embodiments.

Body 200 also includes third blade retaining portion 604 and fourth retaining portion 606 for receiving the anterior and posterior edges of the second blade. This configuration may help maximize available bone graft volume within the implant since the lateral edges of the blades serve as tracks for translation. Specifically, this limits the need for additional track members on the blade that would take up additional volume in the implant. Furthermore, the arrangement of the retaining channels and the associated blade edges results in most of the volume of the retaining channels being filled by the blade edges in the retracted position, which helps prevent any graft material or BGPM (details on the effect and use of bone growth promoting material will be discussed further below) from entering the retaining channels and inhibiting normal blade travel.

Blades and Blade Actuating component

Figure 10:
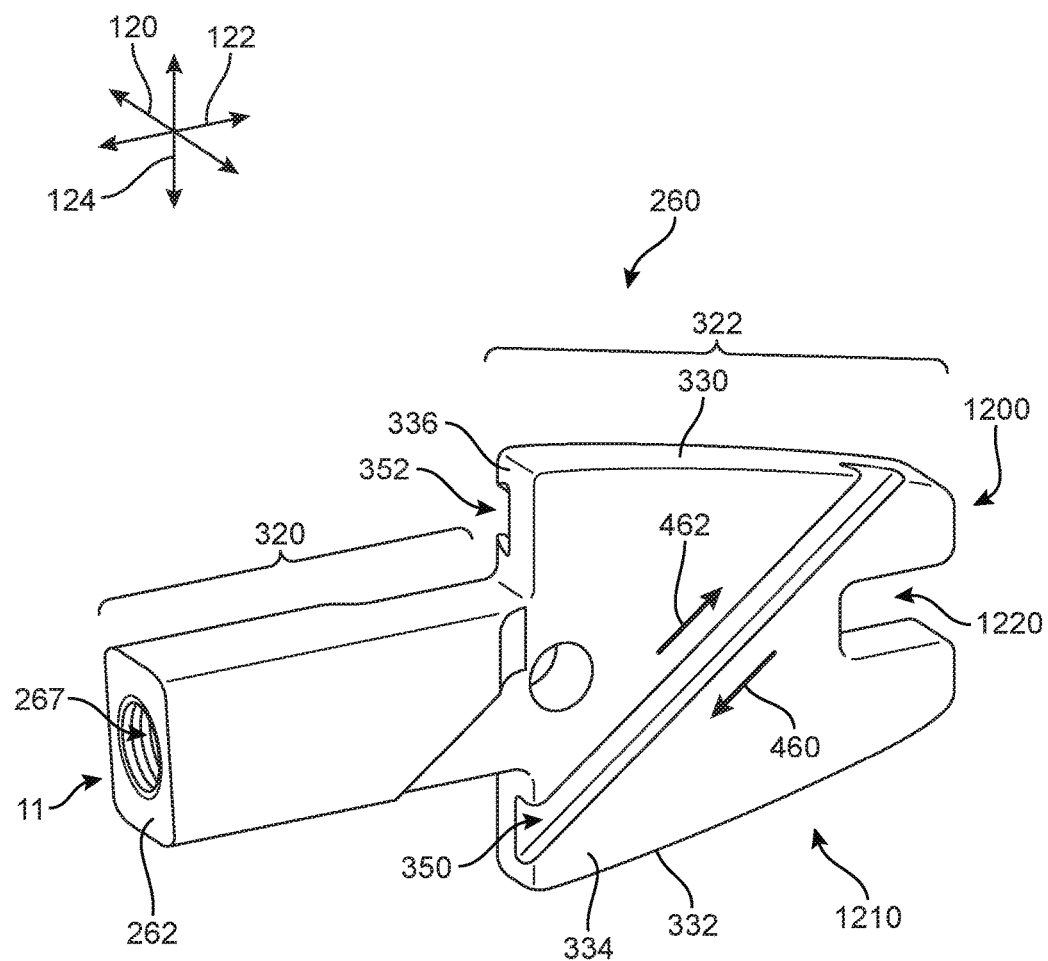
FIG. 10 is a schematic isometric view of an embodiment of a blade actuating component.
Figure 11:
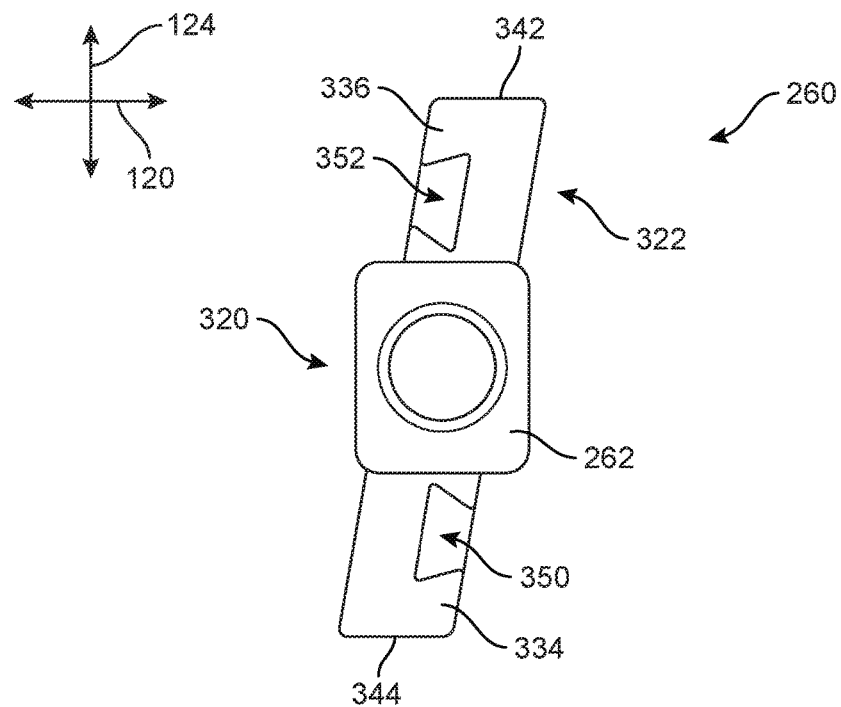
FIG. 11 is a schematic anterior-side view of an embodiment of a blade actuating component.
Figure 12:
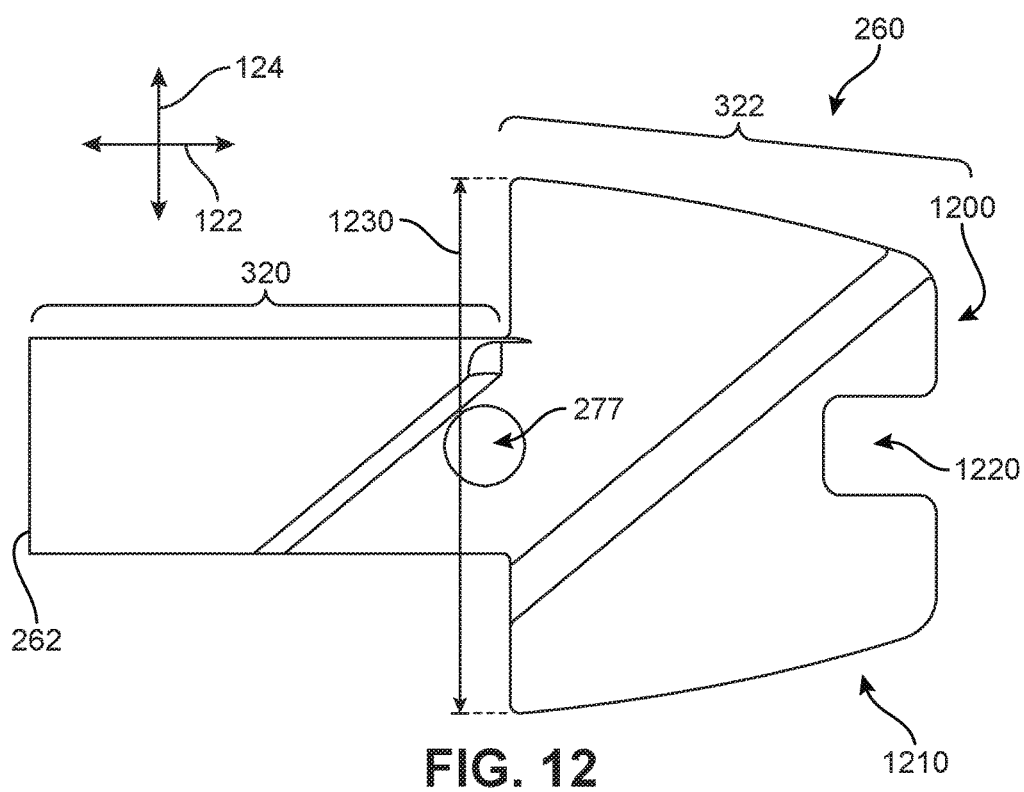
FIG. 12 is a schematic side view of an embodiment of a blade actuating component.

FIG. 10 is an isometric side view of an embodiment of blade actuating component 260. A front or anterior side view of blade actuating component 260 is also shown in FIG. 11, and a lateral side view of blade actuating component 260 is depicted in FIG. 12. Referring to FIGS. 10-12, blade actuating component 260 may include a driven shaft portion 320 and a blade engaging portion 322. Driven shaft portion 320 further includes a driven end 262 along the anterior-most end of driven shaft portion 320.

In some embodiments, driven end 262 can include one or more engaging features. For example, driven shaft portion 320 can include a threaded opening 267 that is accessible from driven end 262, as best seen in FIG. 10. In some embodiments, threaded opening 267 may receive a tool with a corresponding threaded tip. With this arrangement, driven end 262 can be temporarily mated with the end of a tool (see FIG. 37) used to impact blade actuating component 260 and drive the set of blades into adjacent vertebrae. This may help keep both the driving tool and driven end 262 aligned during the impact, as well as reduce the tendency of the driving tool to slip with respect to driven end 262. Using mating features also allows driven end 262 to be more easily "pulled" distally from implant 100, which can be used to retract the blades, should it be necessary to remove the implant or re-position the blades.

In addition, driven shaft portion 320 can be substantially elongated and/or narrow relative to blade engaging portion 322. For example, in FIGS. 10 and 12, driven shaft portion 320 is seen to comprise a substantially elongated rectangular prism. In other words, driven shaft portion 320 has a substantially rounded rectangular cross-sectional shape in the vertical plane. Furthermore, as best seen in FIG. 12, blade engaging portion 322 has a greater width in the direction aligned with vertical axis 124, and includes a generally rectangular shape with a U-shaped or wrench shaped posterior end. The size and shape of blade actuating component 260 allows driven shaft portion 320 to smoothly insert into the guide opening formed in of the body (see FIG. 6) while blade engaging portion 322 is shaped and sized to be positioned in the central opening of the body (see FIG. 7) and configured to receive the blade set.

Furthermore, as will be discussed further below with respect to FIGS. 20 and 21, blade actuating component 260 includes provisions for securing or receiving a portion of the cover within the implant. For example, in FIGS. 10 and 12, blade actuating component 260 includes an actuating posterior end 1200, which includes a receiving portion 1210. Receiving portion 1210 can be sized and dimensioned to receive, fit, or be disposed around a portion of the cover in some embodiments. In one embodiment, receiving portion 1210 comprises a mouth 1220 with two prongs that are spaced apart from one another along vertical axis 124. In some cases, the two prongs can be spaced apart by a width that is substantially similar to the thickness of the cover.

A blade actuating component can include provisions for coupling with one or more blades. In some embodiments, a blade actuating component can include one or more channels. In the exemplary embodiment of FIGS. 10 and 11, blade engaging portion 322 includes a first channel 350 and a second channel 352. First channel 350 may be disposed in a first side surface 334 of blade actuating component 260 while second channel 352 may be disposed in a second side surface 336 of blade actuating component 260.

In addition, referring to FIG. 11, it can be seen that blade engaging portion 322 is oriented diagonally with respect to vertical axis 124. In other words, a superior end 342 of blade engaging portion 322 is offset with respect to an inferior end 344, such that the two ends are not aligned relative to vertical axis 124 when viewed from the anterior side of the component. In some embodiments, this can allow first channel 350 and second channel 352 to be approximately aligned in the vertical direction.

Figure 13:
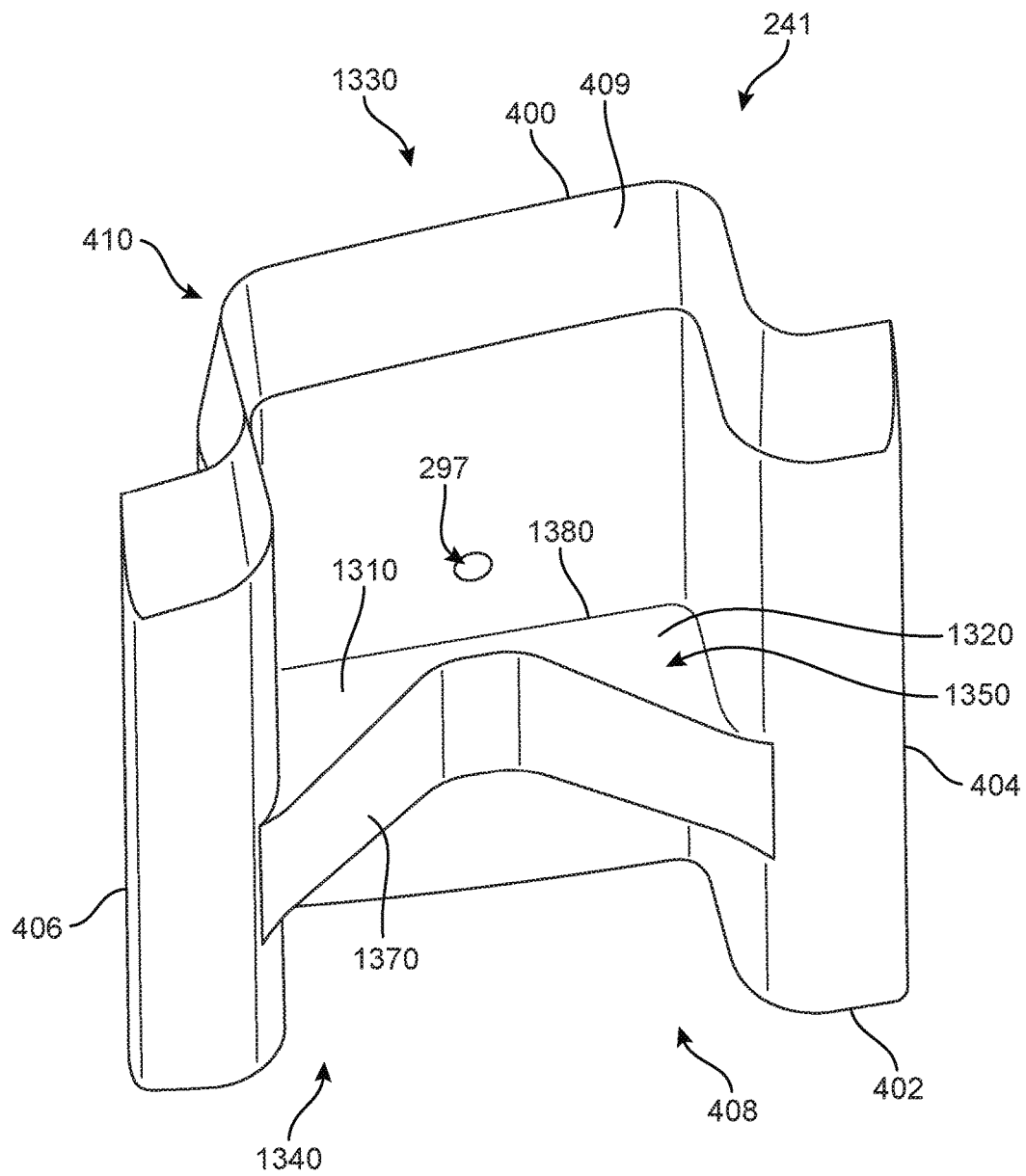
FIG. 13 is a schematic isometric view of an embodiment of a blade.
Figure 14:
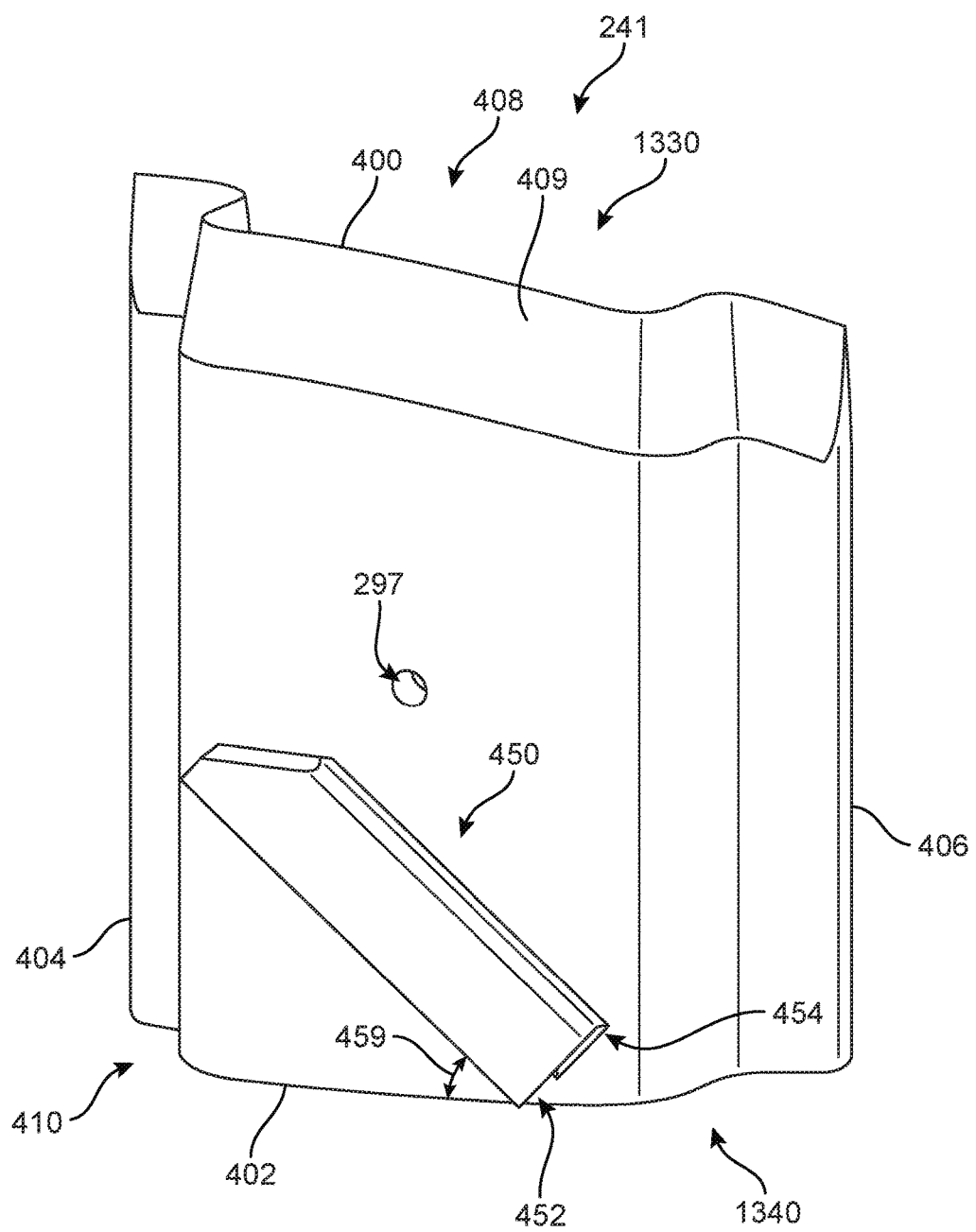
FIG. 14 is a schematic isometric view of an embodiment of a blade.
Figure 15:
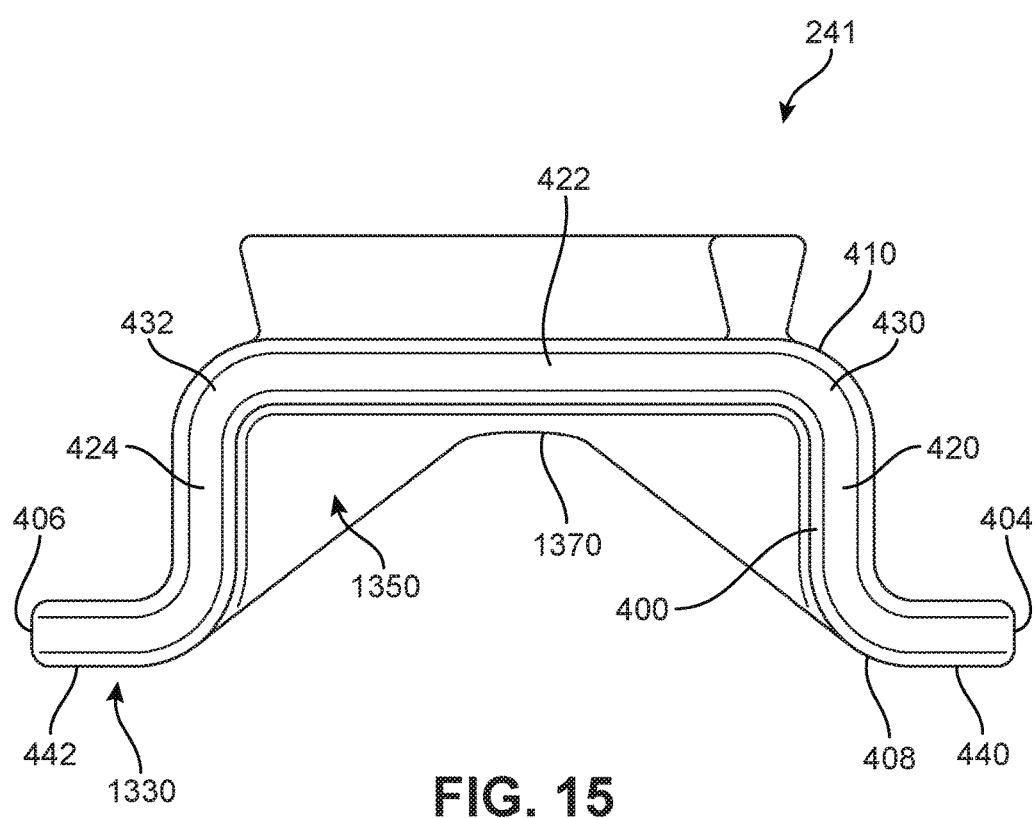
FIG. 15 is a schematic view of an embodiment of a blade.

FIG. 13 is a schematic isometric view of a distal face 408 of first blade 241, FIG. 14 is a schematic isometric view of a proximal face 410 of first blade 241, and FIG. 15 depicts an inferior side 1330 of first blade 241. First blade 241, or simply blade 241, includes an outer edge 400 associated with inferior side 1330 of blade 241, an inner edge 402 associated with a superior side 1340, an anterior edge 404 and a posterior edge 406. These edges bind distal face 408 (i.e., a face oriented in the outwardly-facing or distal direction) and proximal face 410 (i.e., a face oriented in the inwardly-facing or proximal direction).

In different embodiments, the geometry of a blade could vary. In some embodiments, a blade could have a substantially planar geometry such that the distal face and the proximal face of the blade are each parallel with a common plane, as best shown in FIG. 15. In other embodiments, a blade could be configured with one or more bends. In some embodiments, a blade can have a channel-like geometry (ex. "C"-shaped or "S"-shaped). In the embodiment shown in FIG. 15, blade 241 has a U-shaped geometry with flanges. In particular, blade 241 a first channel portion 420, a second channel portion 422 and a third channel portion 424. Here, the first channel portion 420 is angled with respect to second channel portion 422 at a first bend 430. Likewise, third channel portion 424 is angled with respect to second channel portion 422 at second bend 432. Additionally, blade 241 includes a first flange 440 extending from first channel portion 420 at a third bend 434. Blade 241 also includes a second flange 442 extending from third channel portion 424 at a fourth bend 436. This geometry for blade 241 helps provide optimal strength for blade 241 compared to other planar blades of a similar size and thickness, and allowing for greater graft volume.

Furthermore, in some embodiments, blade 241 can include provisions for increasing the support or structural strength of blade 241. In one embodiment, blade 241 includes a bridge portion 1350 that is disposed or formed on distal face 408. Referring to FIG. 13, bridge portion 1350 extends between third bend 434 and fourth bend 436. Bridge portion 1350 can be configured to increase the structural support of blade 2412. In different embodiments, bridge portion 1350 can include features that provide a truss, brace, buttress, strut, joist, or other type of reinforcement to the curved or undulating structure of blade 241. In one embodiment, bridge portion 1350 is disposed nearer to the inner edge relative to the outer edge, such that bridge portion 1350 is offset relative to the distal face of the blade.

In some embodiments, bridge portion 1350 includes a relatively wide U-shaped or curved V-shaped outer sidewall 1370. In FIG. 13, outer sidewall 1370 extends between third bend 434 and fourth bend 436. Furthermore, bridge portion 1350 can have an inner sidewall (disposed on the opposite side of the bridge portion relative to the outer sidewall) that is disposed flush or continuously against the distal surfaces of first channel portion 420, second channel portion 422, and third channel portion 424, represented in FIG. 13 by a U-shaped edge 1380. In one embodiment, the U-shape associated with the inner sidewall or edge of bridge portion 1350 is substantially similar to the U-shape geometry of blade 241.

Bridge portion 1350 can also be substantially symmetrical in some embodiments. For example, in FIG. 13, bridge portion 1350 comprises a first triangular prism portion 1310 joined to a second triangular prism portion 1320 by a central curved portion. Each portion can bolster the structure of the blade, and provide resistance against the pressures applied to a blade by external forces during use of the implant. Thus, bridge portion 1350 can improve the ability of blade 241 to resist external pressures and forces and/or help maintain the specific shape of blade 241.

In the exemplary embodiment, the outer edge 400 is a penetrating edge configured to be implanted within an adjacent vertebral body. To maximize penetration, outer edge 400 may be sharpened so that blade 241 has an angled surface 409 adjacent outer edge 400. Moreover, in some embodiments, anterior edge 404 and posterior edge 406 are also sharpened in a similar manner to outer edge 400 and may act as extensions of outer edge 400 to help improve strength and penetration. It can be understood that, in some embodiments, bridge portion 1350 can also serve to help prevent the blades from extending further outward into a vertebrae downward once they reach the desired deployment extension.

A blade can further include provisions for coupling with a blade actuating component. In some embodiments, a blade can include a protruding portion. In some embodiments, the protruding portion can extend away from a face of the blade and may fit within a channel in a blade actuating component. Referring to FIG. 14, blade 241 includes a protruding portion 450 that extends from proximal face 410. Protruding portion 450 may generally be sized and shaped to fit within a channel of the blade actuating component (i.e., first channel 350 shown in FIG. 11). In particular, the cross-sectional shape may fit within a channel of the blade actuating component. In some cases, the cross-sectional width of protruding portion 450 may increase between a proximal portion 452 and a distal portion 454 allowing protruding portion 450 to be interlocked within a channel as discussed in detail below.

A protruding portion may be oriented at an angle on a blade so as to fit with an angled channel in a blade actuating component. In the embodiment of FIG. 14, protruding portion 450 may be angled with respect to inner edge 402 such that the body of blade 241 is vertically oriented within the implant when protruding portion 450 is inserted within the first channel. In other words, the longest dimension of protruding portion 450 may form a protruding angle 459 with inner edge 402.

Although the above discussion is directed to first blade 241, it may be appreciated that similar principles apply for second blade 242. In particular, in some embodiments, second blade 242 may have a substantially identical geometry to first blade 241. Furthermore, while reference is made to a superior side and inferior side with respect to the first blade, it will be understood that, in some embodiments, the orientation of the second blade can differ such that the inner edge is associated with the inferior side and the outer edge is associated with the superior side.

Figure 16:
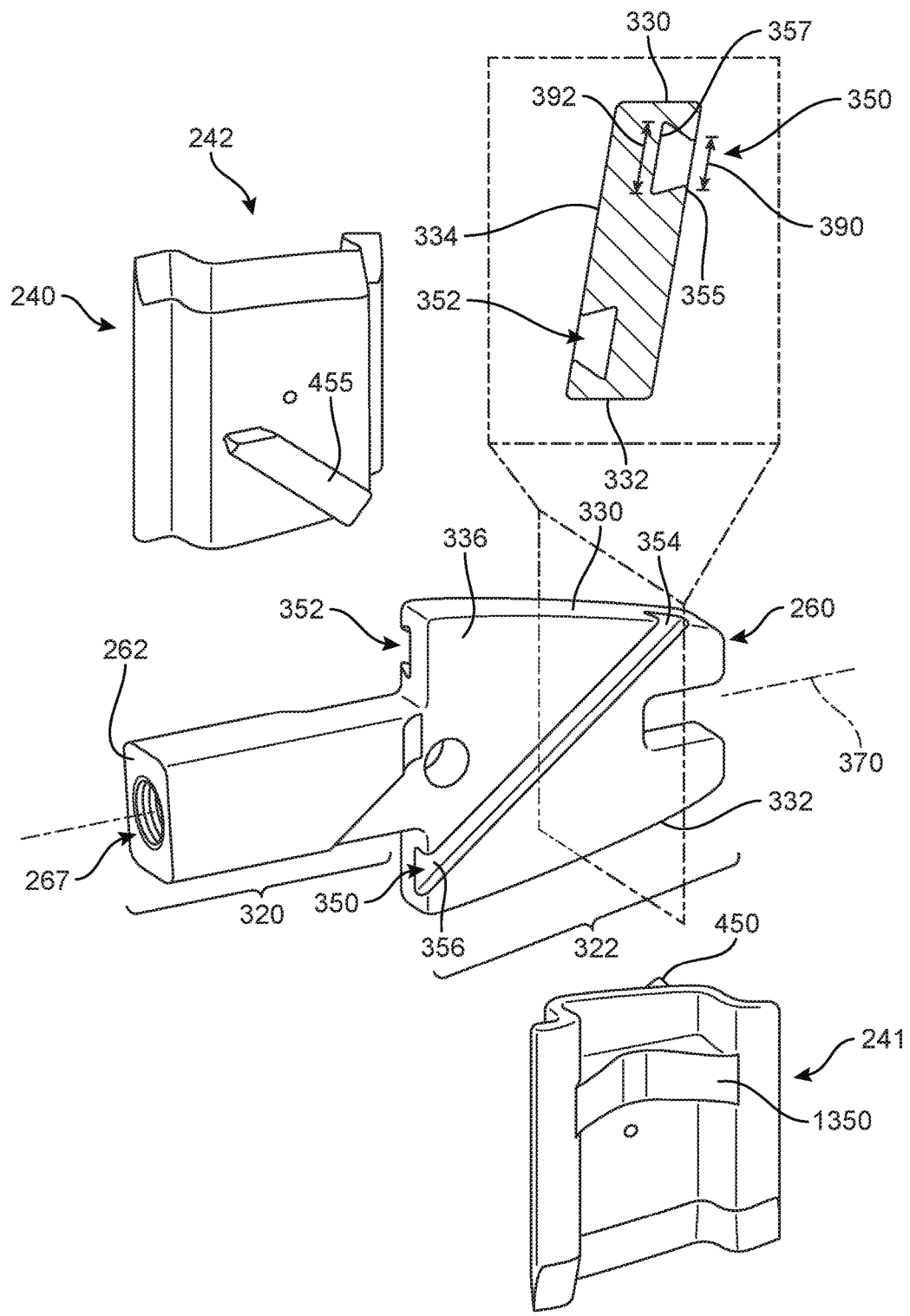
FIG. 16 is a schematic isometric view of an embodiment of a blade actuating component and two corresponding blades.
Figure 17:
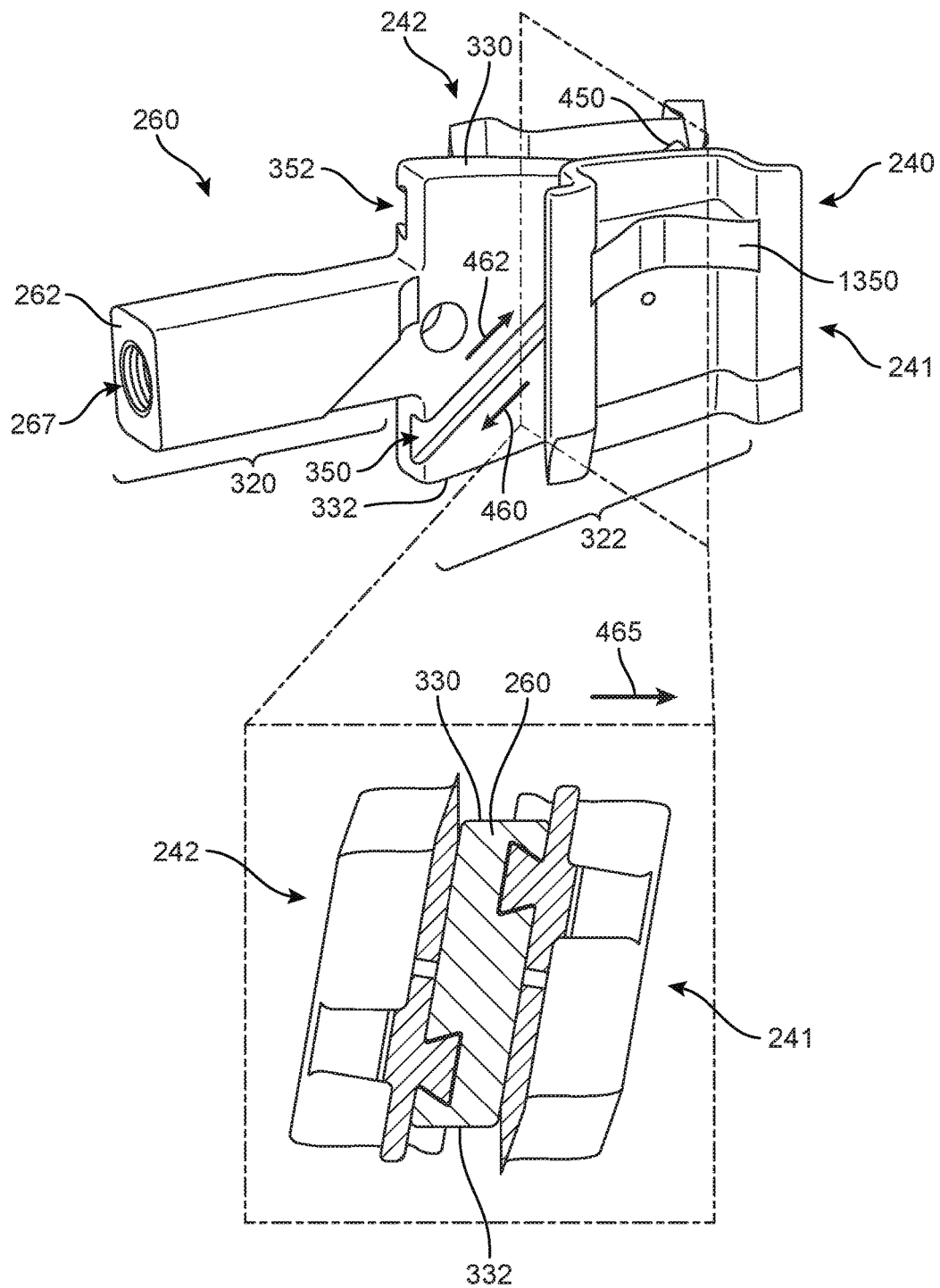
FIG. 17 is a schematic isometric view of the blade actuating component of FIG. 16 coupled with the two corresponding blades.

As noted above, each blade may be associated with the blade engaging portion of the blade actuating component. In FIG. 16, an exploded isometric view is shown with blade actuating component 260, first blade 241, and second blade 242, and in FIG. 17, first blade 241 and second blade 242 are assembled within blade actuating component 260. It can be seen that protruding portion 450 of first blade 241 fits into first channel 350. Likewise, protruding portion 455 of second blade 242 fits into second channel 352. Referring to FIGS. 16 and 17, blade engaging portion 322 may comprise a superior surface 330, an inferior surface 332, a first side surface 334, and a second side surface 336. Here, first side surface 334 may be a first lateral side facing surface and second side surface 336 may be a second lateral side facing side surface.

Each channel that is formed in blade engaging portion 322 is seen to extend at an angle between superior surface 330 and inferior surface 332 of blade engaging portion 322. For example, as best seen in FIG. 16, first channel 350 has a first end 354 open along superior surface 330 and a second end 356 open along inferior surface 332. Moreover, first end 354 is disposed further from driven shaft portion 320 than second end 356. Likewise, second channel 352 includes opposing ends on superior surface 330 and inferior surface 332, though in this case the end disposed at superior surface 330 is disposed closer to driven shaft portion 320 than the end disposed at inferior surface 332.

In different embodiments, the angle of each channel could be selected to provide proper blade extension for varying implant sizes. As used herein, the angle of a channel is defined to be the angle formed between the channel and a transverse plane of the blade actuating component. In the embodiment of FIGS. 16 and 17, first channel 350 forms a first angle with transverse plane 370 of blade actuating component 260, while second channel 352 forms a second angle with transverse plane 370. In the exemplary embodiment, the first angle and the second angle are equal to provide balanced reactive forces as the blades are deployed. By configuring the blades and blade actuating component in this manner, each blade is deployed about a centerline (e.g., transverse plane 370) of the blade actuating component, which helps minimize friction and binding loads between these parts during blade deployment. Additionally, the arrangement helps provide balanced reaction forces to reduce insertion effort and friction.

In different embodiments, the angle of each channel could vary. In some embodiments, a channel could be oriented at any angle between 15 and 75 degrees. In other embodiments, a channel could be oriented at any angle between 35 and 65 degrees. Moreover, in some embodiments, the angle of a channel may determine the angle of a protruding portion in a corresponding blade. For example, protruding angle 459 formed between protruding portion 450 and inner edge 402 of blade 241 (see FIG. 14) may be approximately equal to the angle formed between first channel 350 and transverse plane 370. This keeps the outer penetrating edge of blade 241 approximately horizontal so that the degree of penetration does not vary at different sections of the blade.

Furthermore, as seen in FIG. 16, each channel has a cross-sectional shape that facilitates a coupling or fit with a corresponding portion of a blade. As an example, channel 350 has an opening 355 on first side surface 334 with an opening width 390. At a location 357 that is proximal to opening 355, channel 350 has a width 392 that is greater than opening width 390. This provides a cross-sectional shape for channel 350 that allows for a sliding joint with a corresponding part of first blade 241. In the exemplary embodiment, first channel 350 and second channel 352 are configured with dovetail cross-sectional shapes. In other embodiments, however, other various cross-sectional shapes could be used that would facilitate a similar sliding joint connection with a correspondingly shaped part. In other words, in other embodiments, any geometry for a blade and a blade actuating component could be used where the blade and blade actuating component include corresponding mating surfaces of some kind. In addition, in some embodiments, blade engaging portion 322 may be contoured at the superior and inferior surfaces to resist subsidence and allow maximum blade deployment depth. This geometry may also help to keep the blade engaging portion 322 centered between vertebral endplates. As an example, the contouring of superior surface 330 and inferior surface 332 in the present embodiment is best seen in the enlarged cross-sectional view of FIG. 17.

Each channel may be associated with a first channel direction and an opposing second channel direction. For example, as best seen in FIG. 10, first channel 350 may be associated with a first channel direction 460 that is directed towards superior surface 330 along the length of first channel 350. Likewise, first channel 350 includes a second channel direction 462 that is directed towards inferior surface 332 along the length of first channel 350.

With first protruding portion 450 of first blade 241 disposed in first channel 350, first protruding portion 450 can slide in first channel direction 460 or second channel direction 462. As first protruding portion 450 slides in first channel direction 460, first blade 241 moves vertically with respect to blade actuating component 260 such that first blade 241 extends outwardly on a superior side of the implant to a deployed position (see FIGS. 26-27). As first protruding portion 450 slides in second channel direction 462, first blade 241 moves vertically with respect to blade actuating component 260 such that first blade 241 is retracted within housing 201 of implant 100 (see FIG. 28). In a similar manner, second protruding portion 455 of second blade 242 may slide in first and second channel directions of second channel 352 such that second blade 242 can be extended and retracted from implant 100 on an inferior side (see FIGS. 25-28). By using this configuration, blade actuating component 260 propels both blades in opposing directions thereby balancing the reactive loads and minimizing cantilevered loads and friction on the guide bar.

As shown in the cross section of FIG. 17, the fit between each blade and the respective channel in blade actuating component 260 may be configured to resist motion in directions orthogonal to the corresponding channel directions. For example, with first protruding portion 450 inserted within first channel 350, first blade 241 can translate along first channel direction 460 or second channel direction 462, but may not move in a direction 465 that is perpendicular to first channel direction 460 and second channel direction 462 (i.e., blade 241 cannot translate in a direction perpendicular to the length of first channel 350). Specifically, as previously mentioned, the corresponding cross-sectional shapes of first channel 350 and first protruding portion 450 are such that first protruding portion 450 cannot fit through the opening in first channel 350 on first side surface 334 of blade actuating component 260.

In some embodiments, each protruding portion forms a sliding dovetail connection or joint with a corresponding channel. Using dovetail tracks on the blade actuating component and corresponding dovetail features on the posterior and anterior blades allows axial movement along the angle of inclination while preventing disengagement under loads encountered during blade impaction and retraction. For example, in FIG. 17, first protruding portion 450 forms a sliding dovetail joint with first channel 350. Of course, the embodiments are not limited to dovetail joints and other fits/joints where the opening in a channel is smaller than the widest part of a protruding portion of a blade could be used.

It may be appreciated that in other embodiments, the geometry of the interconnecting parts between a blade and a blade actuating component could be reversed. For example, in another embodiment, a blade could comprise one or more channels and a blade actuating component could include corresponding protrusions to fit in the channels. In such embodiments, both the protruding portion of the blade actuating component and the channels in the blades could have corresponding dovetail geometries.

Body and Cover

Figure 18:
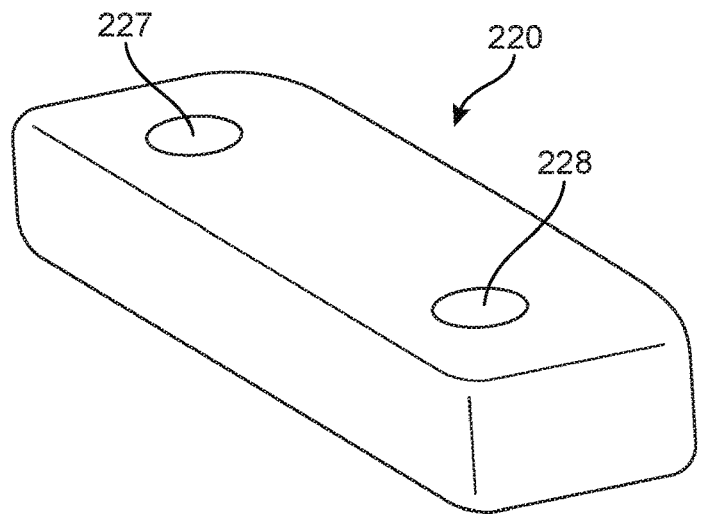
FIG. 18 is a schematic isometric view of a superior side of a cover of an implant, according to an embodiment.
Figure 19:
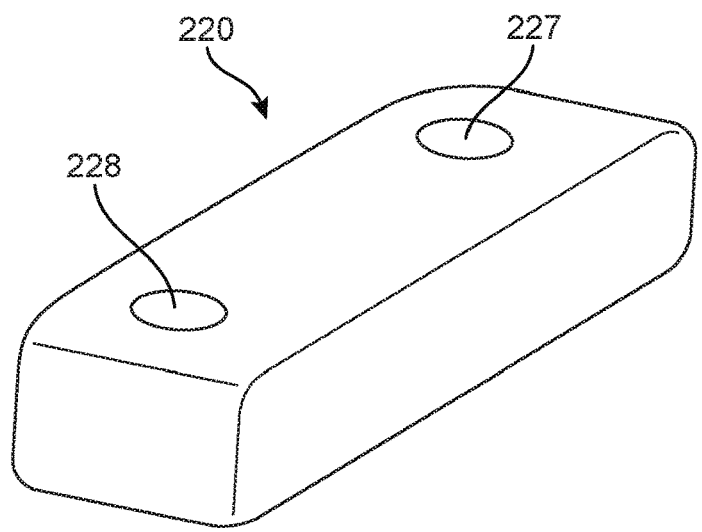
FIG. 19 is a schematic isometric view of an inferior side of the cover of FIG. 13.

As discussed above with respect to FIG. 5, embodiments of implant 100 can include a cover 220 that is configured to close or bridge the posterior opening of body 200 and help secure the various components of implant 100 together. FIG. 18 is a schematic isometric superior-side view of an embodiment of cover 220, and is a schematic isometric inferior-side view of an embodiment of cover 220. Referring to FIGS. 18 and 19, cover 220 includes one or more openings for engaging different parts of implant 100. For example, cover 220 may include a first pin hole 227 and a second pin hole 228 that are configured to receive a first pin and a second pin, respectively (see FIG. 5). Each pin hole can comprise a through-hole that extends from the superior surface to the inferior surface of cover 220, though in other embodiments pin holes can be blind holes. Moreover, first pin hole 227 and second pin hole 228 (shown in FIGS. 18 and 19) of cover 220 may be aligned with corresponding holes in the body, as discussed below.

Figure 20:
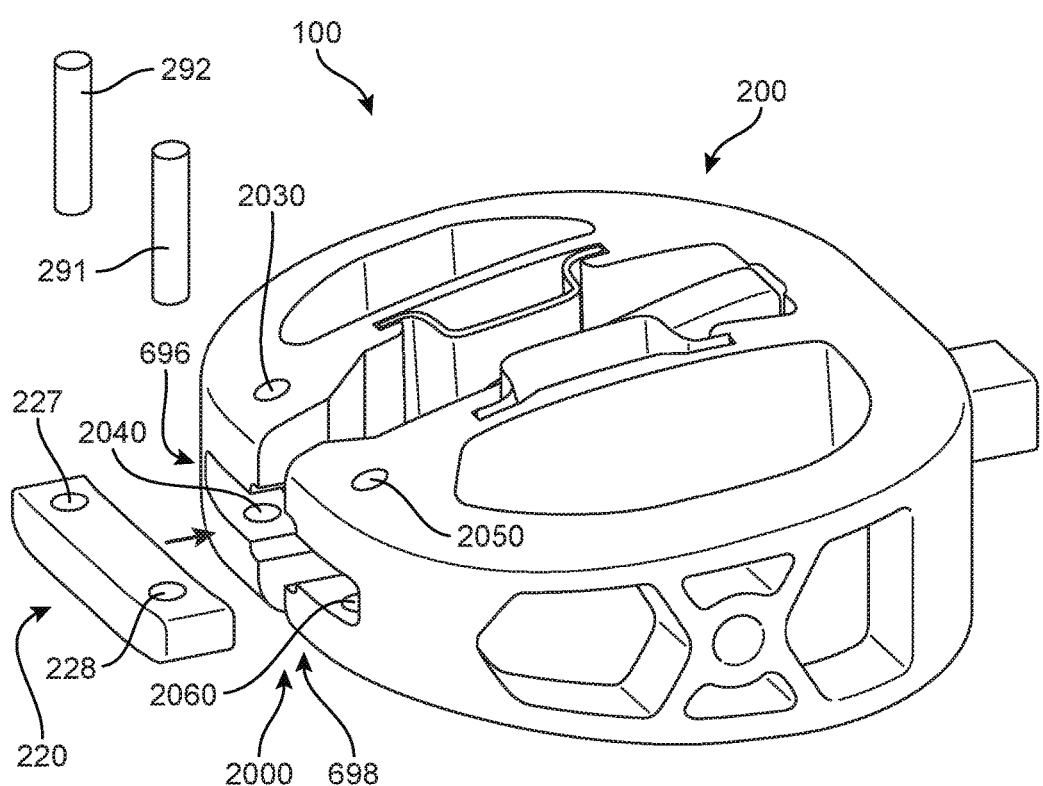
FIG. 20 is a schematic isometric view of an embodiment of a body and a cover for an implant.

FIG. 20 is a schematic isometric exploded view of body 200 and cover 220. FIG. 21 is a schematic isometric assembled view of body 200 and cover 220, together forming housing 201 of implant 100. Specifically, in some embodiments, cover 220 can be inserted into the recesses associated with a posterior end 2000 of body 200. In addition, first pin hole 227 and second pin hole 228 shown in FIG. 20 can be aligned with the pin receiving openings of body 200 comprising between two and four through-hole channels in posterior end 2000. In FIG. 20, first end portion 696 includes a third pin hole 2030 in a superior portion of first end portion 696 and a fourth pin hole 2040 in an inferior portion of first end portion 696. Similarly, second end portion 698 includes a fifth pin hole 2050 in a superior portion of second end portion 698 and a sixth pin hole 2060 in an inferior portion of second end portion 698. When cover 220 is received by body 200, as shown in FIG. 21, third pin hole 2030 and the fourth pin hole are aligned with the first pin hole of cover 220, and fifth pin hole 2050 and the sixth pin hole are aligned with the second pin hole of cover 220. Other embodiments may have a fewer or greater number of pin holes. In some embodiments, body 200 may only include third pin hole 2030 and fifth pin hole 2050, for example. Once cover 220 has been inserted into body 200, first pin 291 and second pin 292 (see FIG. 20) can be inserted into the two sets of pin holes to fasten or secure the body to the cover.

Insertion Position and Deployed Position of Implant

As noted above, the embodiments described herein provide an implant that can move from a first position (the "insertion position"), which allows the implant to maintain a low profile, to a second position (the "impaction position" or the "deployed position"), that deploys the blades and inserts them into the proximal superior and inferior vertebral bodies. While the implant is in the first (insertion) position, the blades of the device may be retracted within the body of the implant (i.e., the blades may themselves be in a "retracted position"). In the second (deployed) position of the implant, the blades extend superiorly (or cranially) or inferiorly (or caudally) beyond the implant and into the vertebral bodies to prevent the implant from moving out of position over time. Thus, the blades themselves may be said to be in an "extended position" or "deployed position". When the blades are deployed, the implant resists left to right rotation and resists flexion and/or extension. It may be appreciated that although the blades may approximately move in vertical directions (i.e., the superior and inferior directions), the actual direction of travel may vary from one embodiment to another. For example, in some embodiments the blades may be slightly angled within the implant and may deploy at slight angles relative to a vertical direction (or to the inferior/superior directions).

Figure 21:
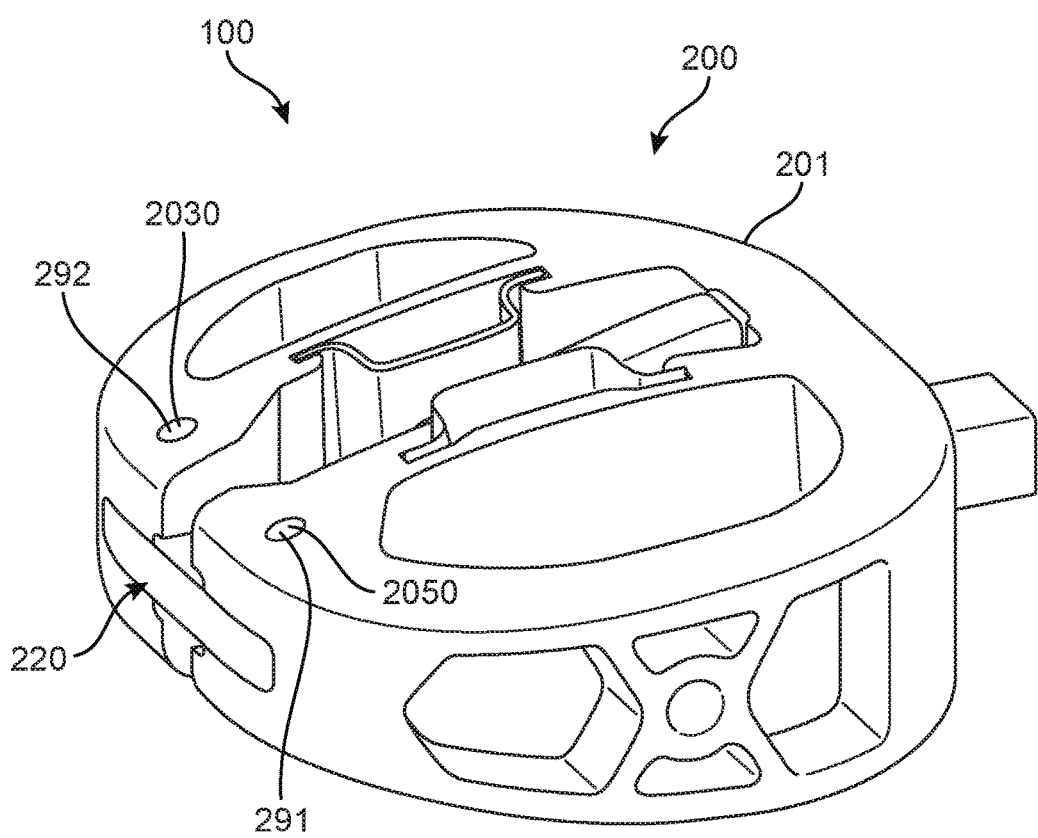
FIG. 21 is a schematic isometric view of an embodiment of a body and a cover for an implant.

FIGS. 4, 21, and 22-24 illustrate several views of implant 100 in different operating modes or operating positions. Specifically, FIG. 4 is a schematic isometric anterior side view of implant 100 in an insertion position. FIG. 21 is a schematic isometric posterior side view of implant 100 in the same insertion position of FIG. 4. Referring to FIG. 4, in the insertion position, driven end 262 of blade actuating component 260 may be disposed distal to the chamber portion of body 200 (i.e., a portion of blade actuating component 260 is disposed or extends through the chamber portion). With implant 100 in the insertion position, first blade 241 and second blade 242 are retracted within housing 201. Thus, as best seen in FIGS. 4 and 21, neither first blade 241 or second blade 242 extend outwardly (distally) from superior side 130 or inferior side 140, respectively, of implant 100. In this insertion position, implant 100 has a compact profile and can be more easily maneuvered into place in the excised disc space between adjacent vertebrae.

Figure 22:
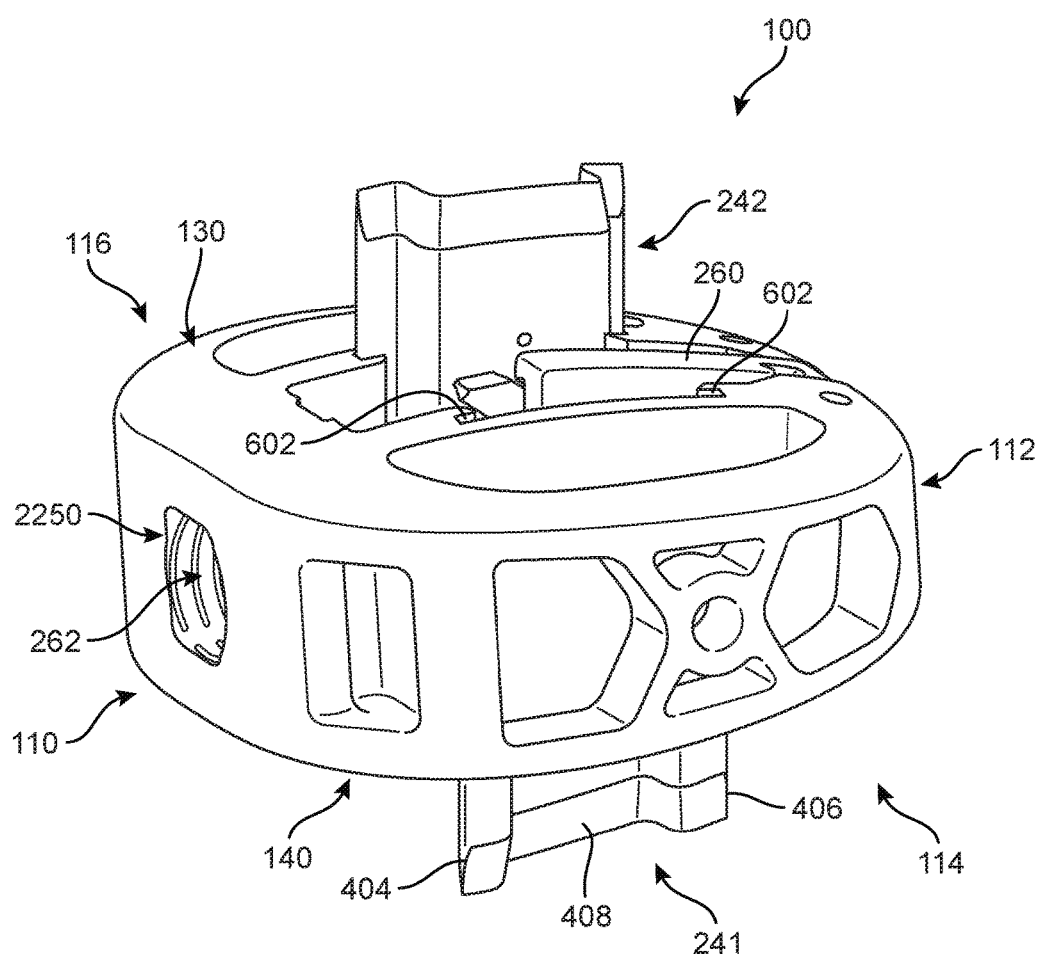
FIG. 22 is a schematic isometric view of an implant in a deployed position.
Figure 23:
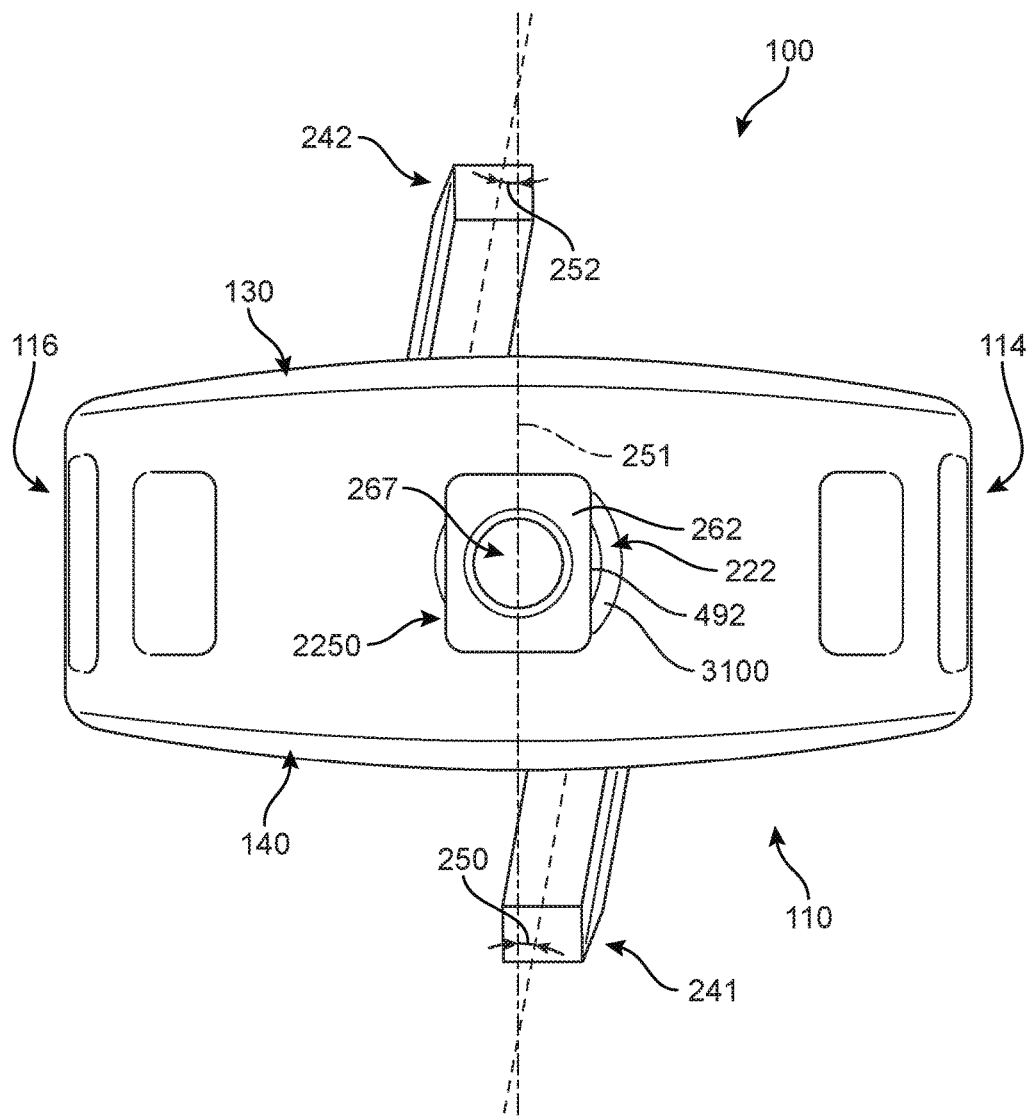
FIG. 23 is a schematic anterior-side view of an implant in a deployed position.
Figure 24:
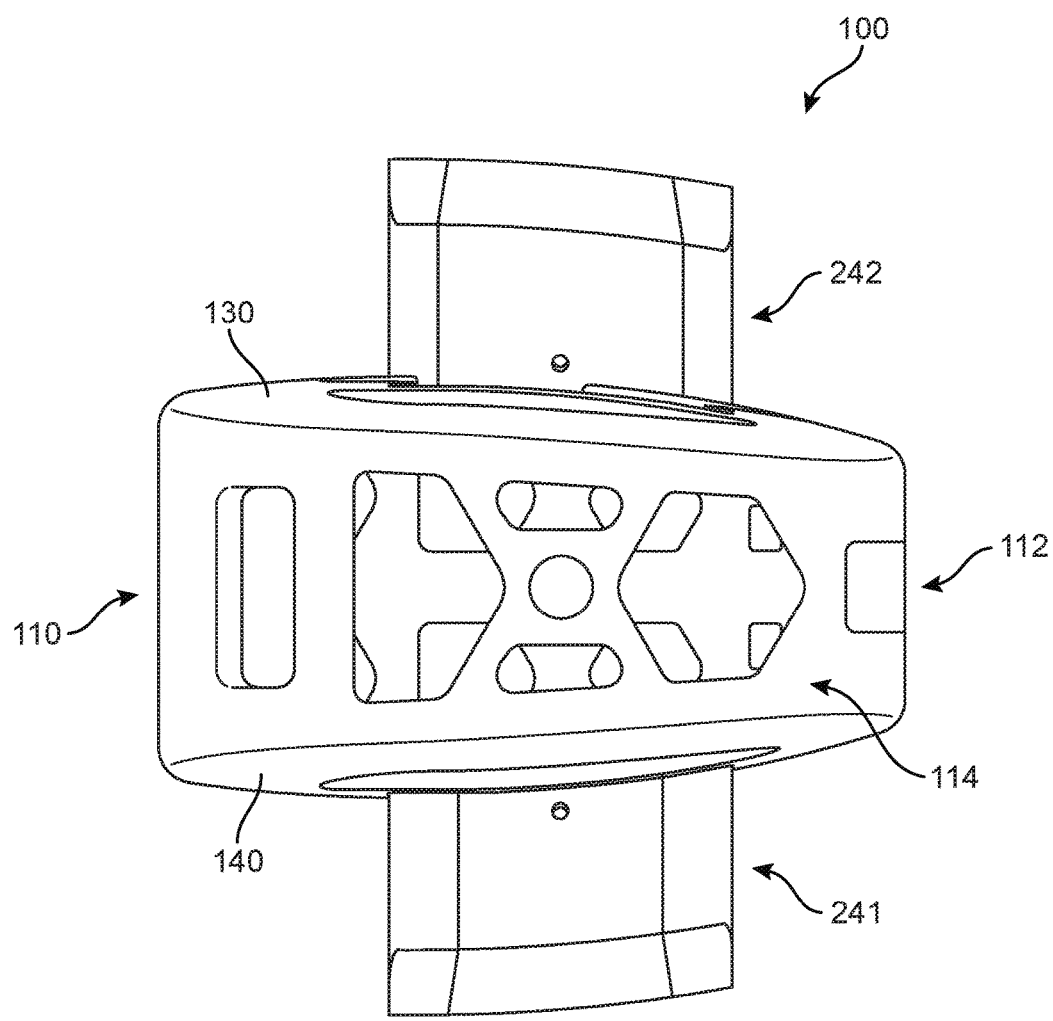
FIG. 24 is a schematic lateral-side view of an implant in a deployed position.

FIG. 22 is a schematic isometric view of implant 100 in a deployed position. FIG. 23 is a schematic anterior side view of implant 100 in the same deployed position of FIG. 22. FIG. 24 is a schematic lateral side view of implant 100 in the same deployed position of FIG. 23. Referring to FIG. 23, in the deployed position, driven end 262 of blade actuating component 260 may be disposed proximally to an anterior opening 2250 formed in the outer periphery of body 200 (i.e., the entirety of blade actuating component 260 is disposed within implant 100). With implant 100 in the deployed position, first blade 241 and second blade 242 are extended outwards from superior side 130 and inferior side 140, respectively, so as to be inserted into adjacent vertebral bodies. Furthermore, each blade remains positioned in the central hollow region of the body in both the retracted and extended positions. For example, an inner edge of each blade is disposed in a central hollow region of the housing in the retracted position, and the inner edge of the blade remains in the central hollow region in the extended position.

In some embodiments, one or more blades could be deployed at a slight angle, relative to the normal directions on the superior and inferior surfaces of the implant. In some embodiments, one or more blades could be oriented at an angle between 0 and 30 degrees. In other embodiments, one or more blades could be oriented at an angle that is greater than 30 degrees. In the exemplary embodiment shown in FIG. 23, first blade 241 and second blade 242 are both oriented at a slight angle from normal axis 251. Specifically, first blade 241 forms a first angle 250 with normal axis 251 and second blade 242 forms a second angle 252 with normal axis 251. In one embodiment, first angle 250 and second angle 252 are both approximately 10 degrees. Angling the blades in this way may help keep first blade 241 and second blade 242 approximately centered in the adjacent vertebrae upon deployment. In an exemplary embodiment, the common anterior implant blade angle is chosen to keep the blades close to the centerline of the vertebral body to minimize rotational loads on the vertebral bodies during blade deployment and also to provide an optional cover plate screw clearance. In addition, it can be seen in FIG. 23 that the outer edge of each blade is positioned toward a central region of the implant when the blade is deployed, such that the outer edge is positioned centrally relative to the housing in the extended position.

The extension of each blade could vary in different embodiments. In some embodiments, a blade could extend outwardly by a length between 0 and 100% of the depth of an implant. In still other embodiments, combined blade height could extend outwardly by a length between 100 and 130% of the depth of an implant. In the exemplary embodiment shown in FIGS. 22-24, first blade 241 and second blade 242 combined may be coverable of extending outwardly from implant 100 by an amount equal to 110% of the depth of implant 100. This can be done while still keeping the blades fully retracted within implant 100 since the blades are guided by two robust parallel tracks in body 200 and also by angled cross channels in blade actuating component 260, thus constraining all six axes of motion. In other embodiments, the combined blade height at deployment could be less than 100%. In one embodiment, the implant could be designed so that the combined blade height is less than 10 mm to reduce the risk of fracturing the adjacent vertebral bodies. In another embodiment, the implant has a combined blade height of 6 mm or less.

Furthermore, as disclosed in the "Implant With Deployable Blades" application, in some embodiments, implant 100 can use a three-point attachment configuration for each of first blade 241 and second blade 242. Specifically, each blade is received along its lateral edges by two blade retaining portions, and also coupled to blade actuating component 260 using the dovetail connection described above. In other words, anterior edge 404 of first blade 241 is received within the first blade retaining channel of first blade retaining portion 600. Posterior edge 406 of first blade 241 is received within a second retaining channel of second blade retaining portion 602. Moreover, distal face 408 of first blade 241 remains unattached to any other elements of implant 100. Not only does first blade 241 remain unattached along distal face 408, but the entirety of distal face 408 between anterior edge 404 and posterior edge 406 is spaced apart from (i.e., not in contact with) all other elements of implant 100. Further, second blade 242 is likewise attached at its lateral edges to corresponding blade retaining portions and also coupled to blade actuating component 260 using a sliding dovetail connection. Thus, first blade 241 and second blade 242 are held in implant 100 using a three-point attachment configuration that may limit unwanted friction on first blade 241 and second blade 242 during impaction. It may be appreciated that the fit between each blade and each blade retaining channel may provide sufficient clearance to allow for translation of the blades along the retaining channels. In other words, the fit may not be so tight as to impede movement of the lateral edges within the retaining channels.

In different embodiments, the cross-sectional geometry of channels in one or more blade retaining portions could vary. In some embodiments, the cross-sectional geometry could be rounded. In the embodiments disclosed herein, first blade retaining portion 600 (see FIG. 22) has a rectangular blade retaining channel. This rectangular geometry for the blade tracks or channels and tolerance allows for precise axial travel without binding from actuation ramp angular variations. In some embodiments, the posterior edge and anterior edge of each blade may remain in the tracks or channels of each blade retaining portion while the blades are retracted to prevent bone graft material from restricting free deployment of the blades.

Using an interlocking joint, such as a dovetail sliding joint, to connect the blades and a blade actuating component helps prevent the blades from decoupling from the blade actuating component during impact. Additionally, with an interlocking joint the blade actuating component can be used to retract the blades.

Figure 26:
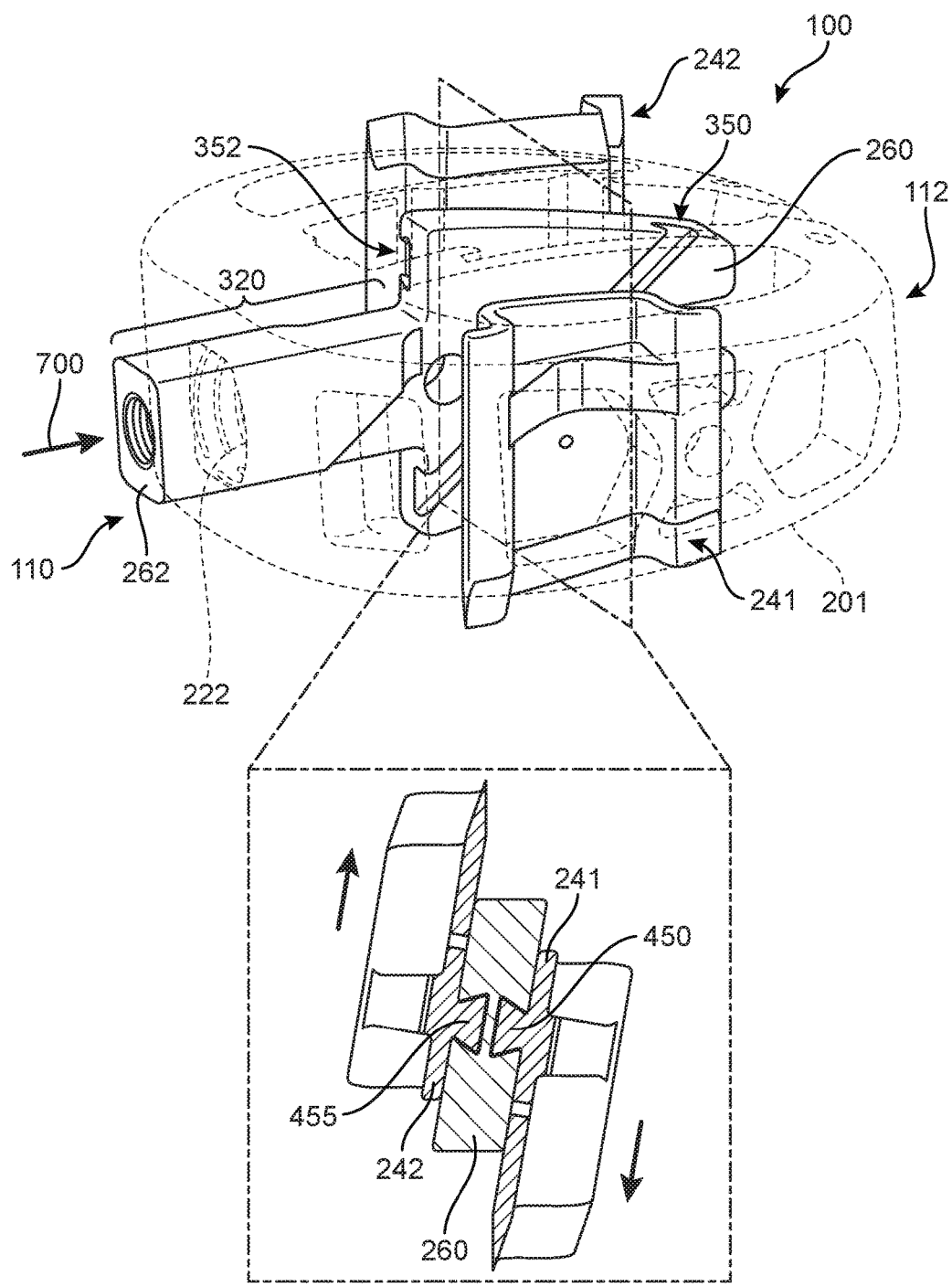
FIG. 26 is a schematic isometric view of the implant of FIG. 25 in an intermediate position between the insertion position and the deployed position here, including a cross-sectional view of the several components.
Figure 27:
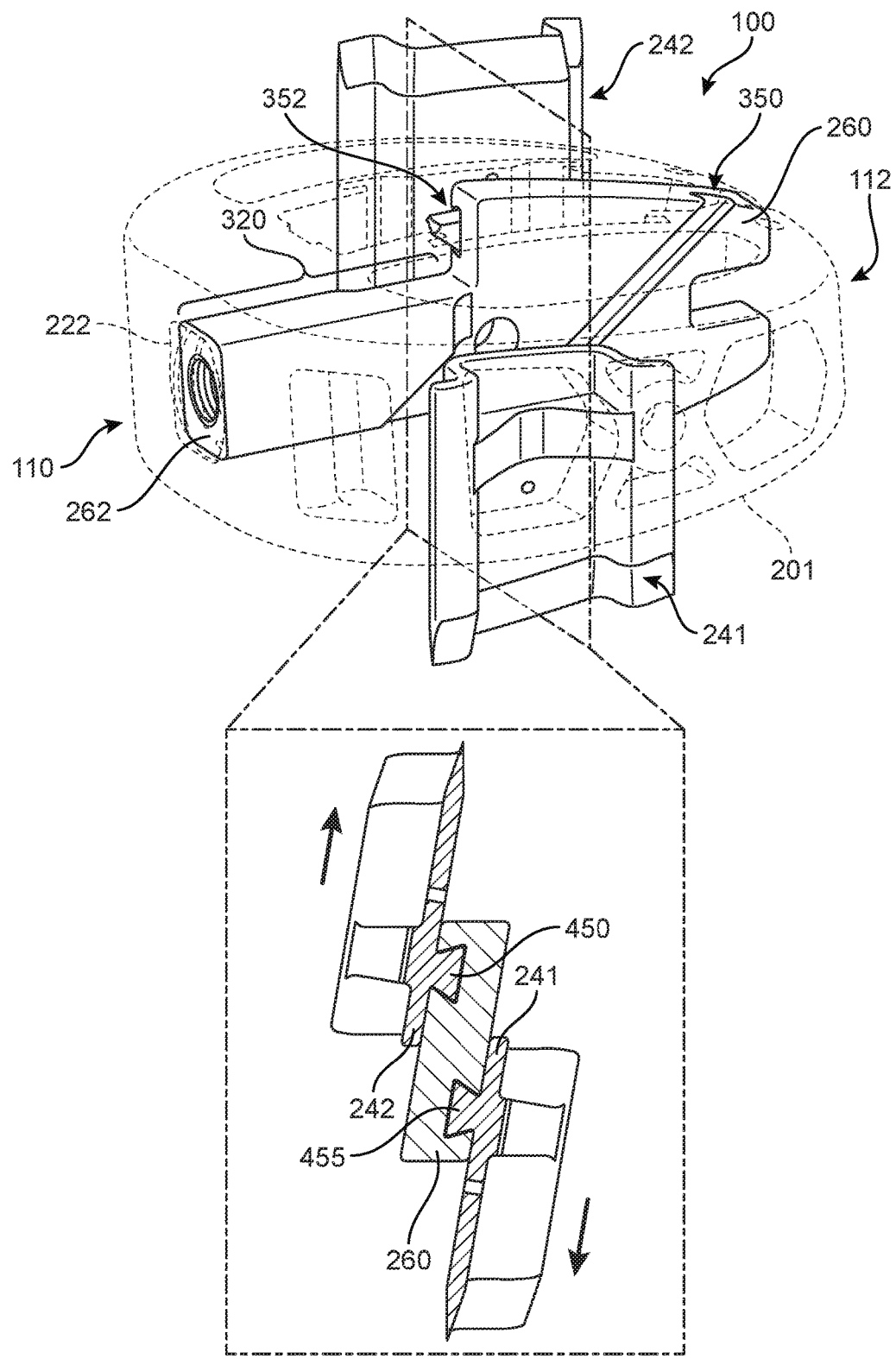
FIG. 27 is a schematic isometric view of the implant of FIG. 25 in a deployed position, including a cross-sectional view of the several components.
Figure 28:
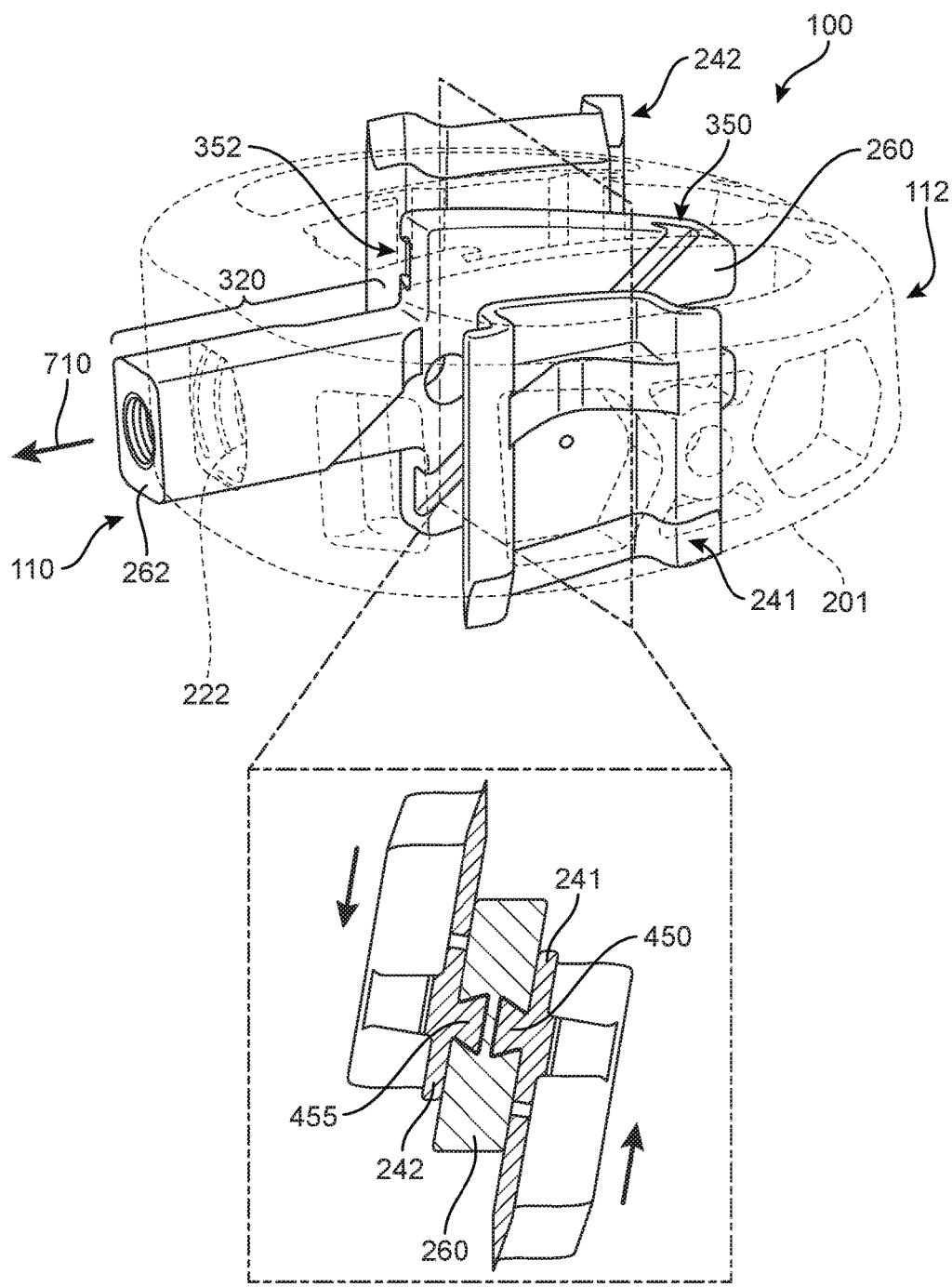
FIG. 28 is a schematic isometric view of the implant of FIG. 25 in an intermediate position, including a cross-sectional view of the several components.

FIGS. 25-28 illustrate several schematic views of implant 100 during an impact sequence (FIGS. 25-27) as well as during a step of retracting the blades (FIG. 28). In FIGS. 25-28, housing 201 of implant 100 is shown in phantom to better show blade actuating component 260, first blade 241 and second blade 242. Also, each of FIGS. 25-28 include cross-sectional views of a section of blade actuating component 260, first blade 241 and second blade 242 to better illustrate the coupling between these parts during actuation.

Figure 25:
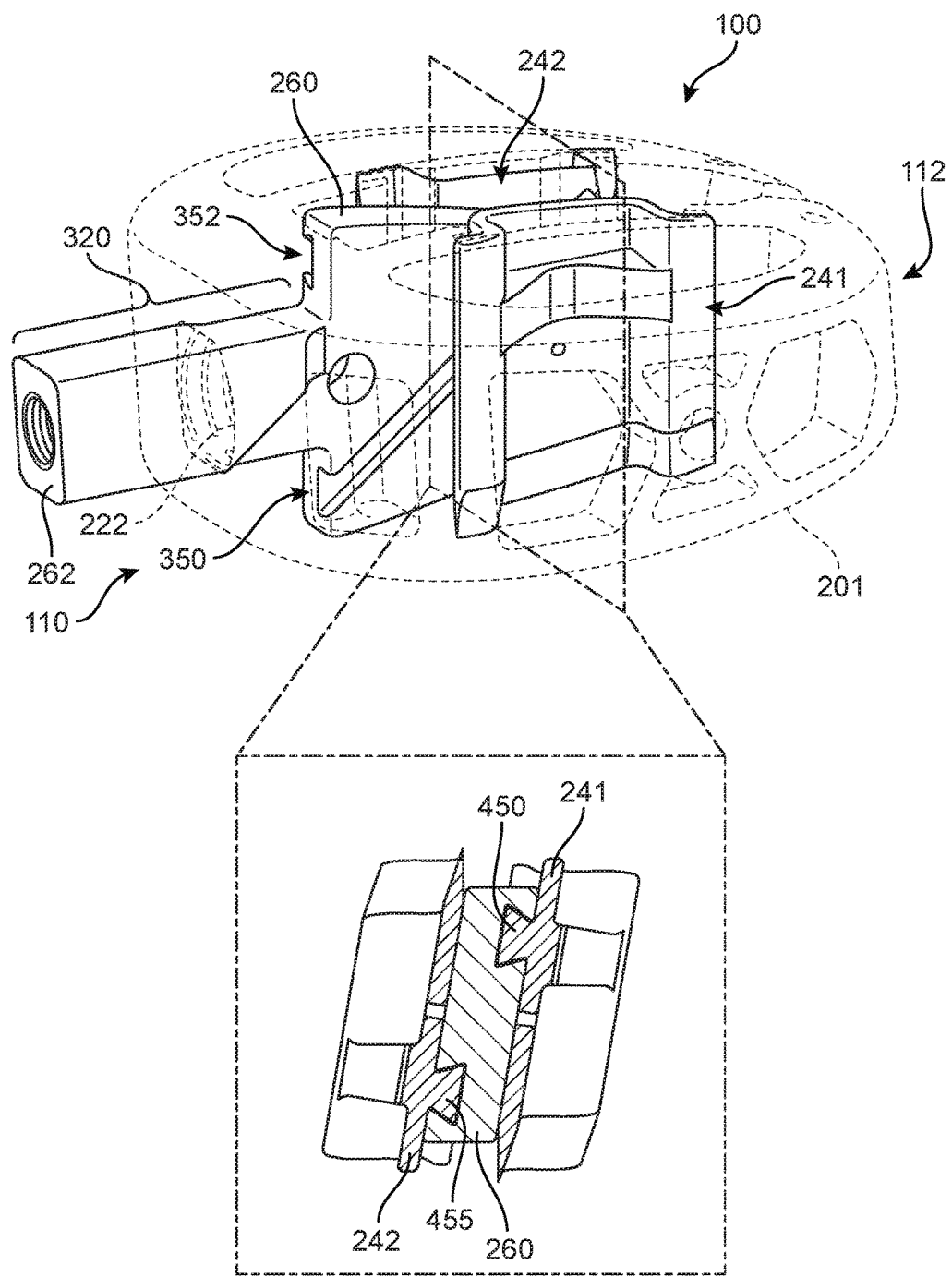
FIG. 25 is a schematic isometric view of an implant in an insertion position, including a cross-sectional view of several components, according to an embodiment.

In FIG. 25, implant 100 is in the insertion position, with first blade 241 and second blade 242 fully retracted within housing 201. Next, as seen in FIG. 26, an impacting force 700 is applied to driven end 262 of blade actuating component 260. As blade actuating component 260 is translated towards posterior side 112 of implant 100, blade actuating component 260 applies forces to first blade 241 and second blade 242 along first channel 350 and second channel 352, respectively. Specifically, the orientation of first channel 350 is such that first blade 241 is forced towards the inferior side of implant 100. Likewise, the orientation of second channel 352 is such that second blade 242 is forced towards the superior side of implant 100. However, in other embodiments, the channel orientations can be switched such that first blade 241 is forced towards the inferior side of implant 100 and second blade 242 is forced towards the superior side of implant 100.

Furthermore, the interlocking connection between first protruding portion 450 and first channel 350 (as well as between second protruding portion 455 and second channel 352) means that both blades remain coupled to the motion of blade actuating component 260 at all times. It should be noted that since both blades are restricted from moving in a longitudinal direction, the resulting motion of each blade is purely vertical. Moreover, using the dovetail shaped protruding portions for each blade means the protruding portions are both lifting at the center line to limit any cocking force or rotational moments that could result in increased (friction) resistance to motion or binding of these moving parts.

Using this configuration, the forces deploying the blades are balanced through the blade actuating component 260 in order to minimize friction and binding between driven shaft portion 320 and the guide opening in body 200 (see FIG. 6), which helps to guide blade actuating component 260 and keep its motion restricted to directions parallel to the longitudinal axis (see FIG. 2).

In FIG. 27, implant 100 has been placed in the fully deployed position, with both first blade 241 and second blade 242 fully extended from implant 100. As seen in the cross-sectional view, both first blade 241 and second blade 242 remain coupled with blade actuating component 260 when implant 100 is in the fully deployed position. Because of this coupling, the motion of blade actuating component 260 can be reversed to retract first blade 241 and second blade 242, as shown in FIG. 28.

It may be appreciated that in some embodiments a blade actuating component (e.g., blade actuating component 260) may function to support adjacent vertebral bodies. This is can be accomplished by using a blade actuating component with a height similar to the height of the outer support structure so that the superior and inferior surfaces of the blade actuating component may come into contact with the vertebral bodies following implantation. Since the blade actuating component functions as a load bearing structure within the implant, this may free up additional space in the implant otherwise occupied by additional support structures, thereby increasing the internal volume available for bone graft or BGPMs.

Referring to FIG. 28, driven end 262 of blade actuating component 260 may be pulled in an opposing direction to the motion shown in FIG. 26. For example, in some embodiments a delivery tool can be coupled to driven end 262 using a threaded connector. Then, as the tip of the delivery tool is retracted a retracting or pulling force 710 may be applied to drive end 262. As blade actuating component 260 (and specifically, blade engaging portion 322) is pulled towards anterior side 110 of implant 100, blade actuating component 260 applies forces to first blade 241 and second blade 242 along first channel 350 and second channel 352, respectively. Specifically, the orientation of first channel 350 is such that first blade 241 is forced towards the superior side of implant 100. Likewise, the orientation of second channel 352 is such that second blade 242 is forced towards the inferior side of implant 100. Although not shown, applying sufficient force at driven end 262 may result in full retraction of first blade 241 and second blade 242 so that implant 100 is returned to the insertion position shown in FIG. 25.

As noted above, body 200 may include guide opening 222 that receives a portion of blade actuating component 260. When the implant is in the deployed position, the driven shaft portion can be disposed securely in the chamber portion. In some embodiments, the chamber portion of guide opening 222 may have a shape that matches the cross-sectional shape of a driven shaft portion of a blade actuating component. In some embodiments, both the chamber portion and the driven shaft portion of the blade actuating component have rectangular cross-sectional shapes (see FIGS. 9 and 11). This configuration may allow axial motion, but control rotational and angular loads that could result during blade impaction.

Locking Screw

Figure 29:
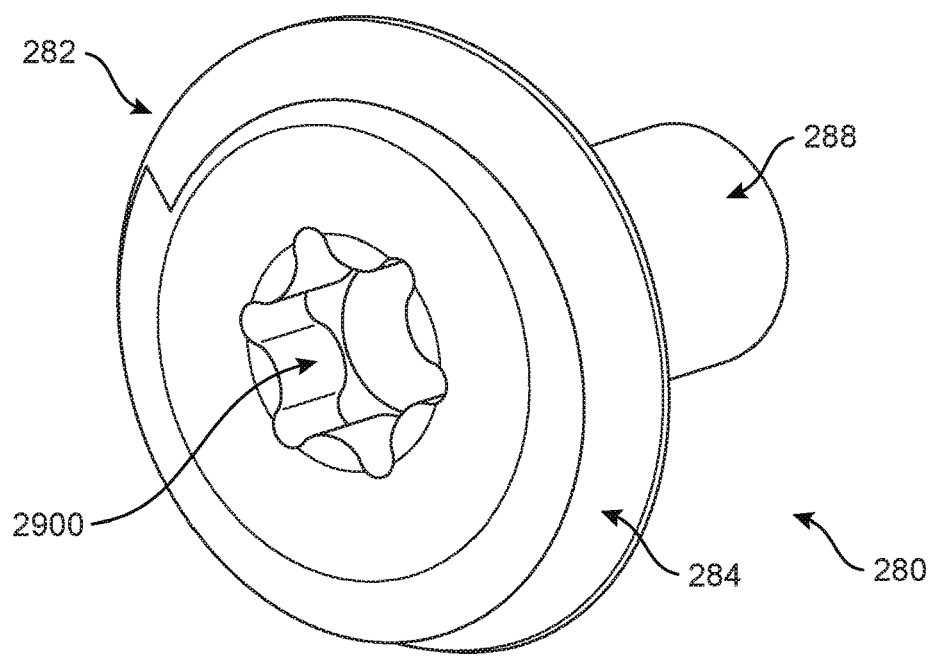
FIG. 29 is a schematic isometric view of a locking screw according to an embodiment.
Figure 30:
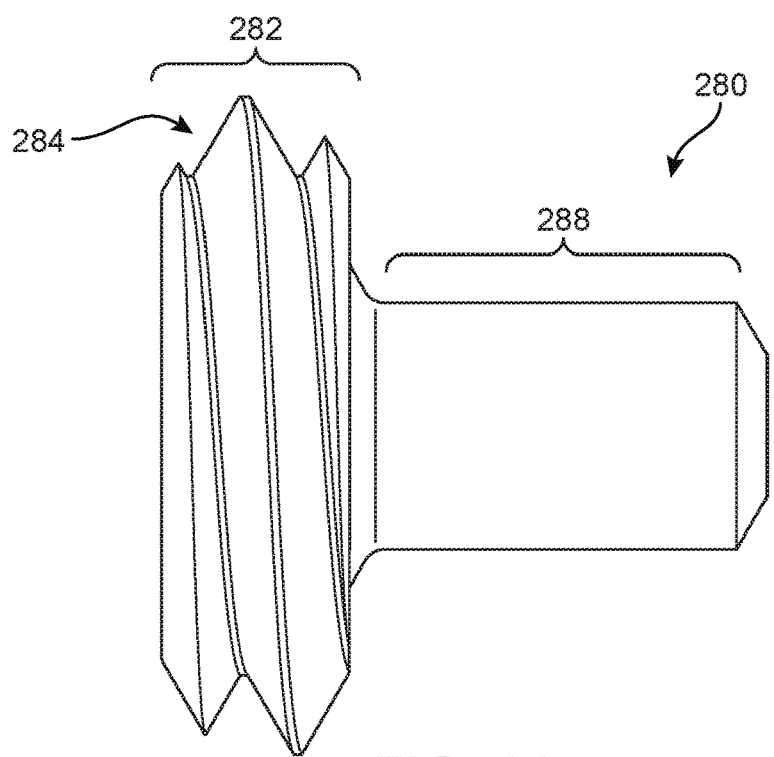
FIG. 30 is a schematic side view of the locking screw of FIG. 29.

FIGS. 29 and 30 illustrate two schematic views of locking screw 280, according to an embodiment. Locking screw 280 can be a type of threaded fastener in some embodiments. In FIG. 29, locking screw 280 includes a flanged head 282 with a threaded segment portion 284 and further includes a substantially smooth and elongated body portion 288. Threaded segment portion 284 is sized and dimensioned to engage with the grooved portion of the body (see FIG. 33 below). Flanged head 282 can also include a receiving recess 2900 which can engage with a driving tool in order to secure the locking screw within the implant. Thus, although body portion 288 is disposed within threaded opening of the blade actuating component when the screw lock is secured, body portion 288 need not engage or lock with the threading associated with the threaded opening.

Implant 100 can include provisions for securing the implant 100 in the deployed position. Referring to the exploded isometric view of FIG. 31, guide opening 222 can include a grooved portion 3100 that is formed directly adjacent to the chamber portion. Grooved portion 3100 can have a round cross-sectional shape in the vertical plane, and has a wider diameter relative to the diameter or width of the chamber portion. The diameter of grooved portion 3100 can be configured to mate with the diameter of the flanged head. In one embodiment, grooved portion 3100 is disposed directly adjacent to the outermost anterior periphery of guide opening 222. As locking screw 280 is inserted into the anterior side of guide opening 222 (see FIG. 32), threaded segment portion 284 that extends around flanged head 282 of locking screw 280 can engage with grooved portion 3100, securing locking screw 280 to body 200. When in this position, body portion 288 of locking screw 280 can also be disposed through the passageway of threaded opening 267 of blade actuating component 260. As shown best in the partial cross-sectional view of FIG. 32, when implant 100 is in the deployed position, a portion of driven shaft portion 320 is disposed within chamber 492 of guide opening 222, primarily comprising the portion of driven shaft portion 320 that includes threaded opening 267. Furthermore, flanged head 282 of locking screw 280 extends from anterior opening 2250 through grooved portion 3100, and body portion 288 of locking screw 280 extends through threaded opening 267 of driven shaft portion 320. Flanged head 282 is prevented from moving further into guide opening 222 because of the larger diameter of flanged head 282 relative to body portion 288. Thus, it can be understood that the insertion of the implant and the deployment of the blades of the implant occur through the engagement of an insertion tool within only a single guide opening 222, improving surgical efficiency and safety.

Alternate Blade Actuating Component

Figure 33:
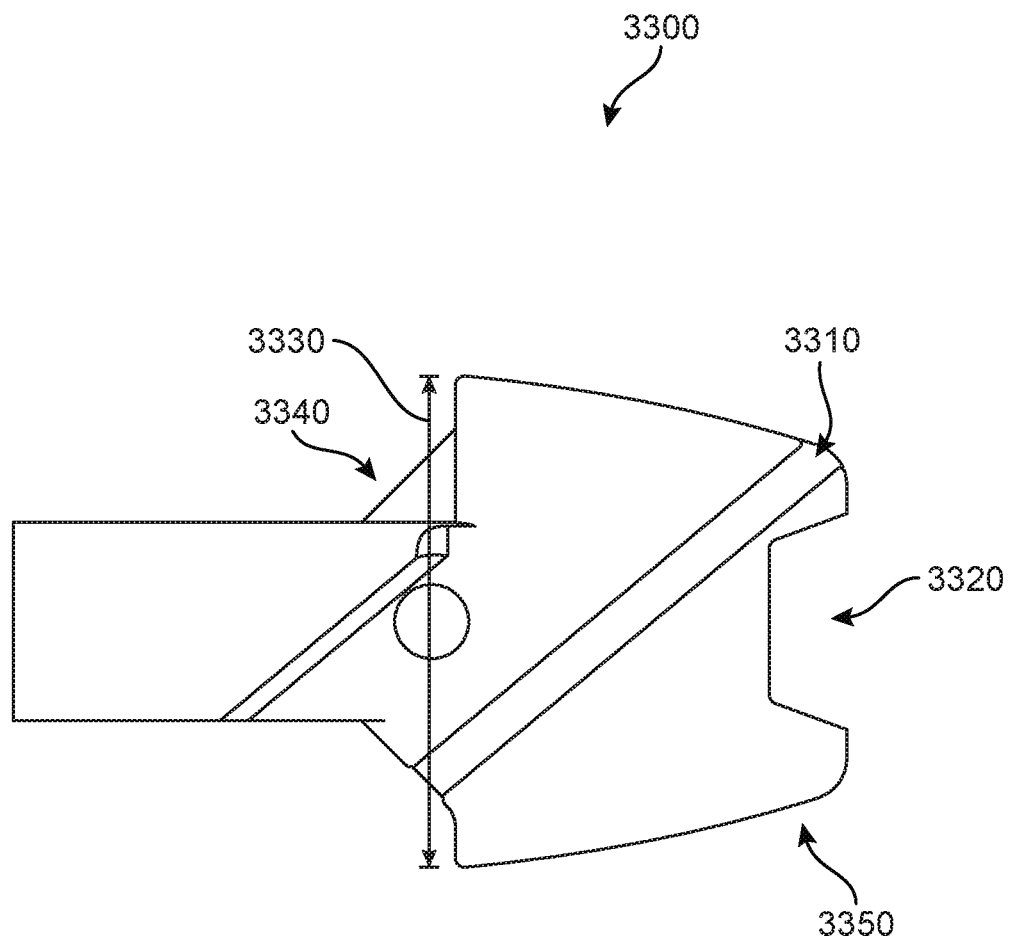
FIG. 33 is a schematic lateral-side view of a blade actuating component for an implant, according to another embodiment.

In different embodiments, an implant can utilize different types of components to provide the features and functions described herein. In some embodiments, the features of blade actuating component can be adjusted in order to facilitate the use of implant with a variety of surgical requirements. For example, in some embodiments, an alternate embodiment of a second blade actuating component ("second actuating component") 3300 can be placed within the housing of the body, as shown in FIG. 33. In FIG. 33, second actuating component 3300 is configured with a receiving portion 3350 with a mouth 3320 that is greater in width than the embodiment of the actuating blade component presented above. Adjustments to the size of a mouth in the receiving portion of a blade actuating component can correspond to changes in the dimensions or shape of a cover, bridge piece, or cap that is used in the implant.

In addition, to allow an implant to withstand varying forces and work with different blade types, the height and/or other dimensions of the blade engaging portion can be increased or decreased. For example, in FIG. 12, blade actuating component 260 has a first maximum height 1230, and in FIG. 33, second actuating component 3300 has a second maximum height 3330. First maximum height 1230 is less than second maximum height 3330, such that blade actuating component 260 can be inserted into a smaller region of the human body. However, when the blades being used must be increased in size, the greater height of second actuating component 3300 provides the structural support to the device. In addition, second actuating component 3300 includes diagonal portions 3340 disposed toward the center of the actuating component that can extend the length of channels 3310 and support additional blade weight. In some embodiments, diagonal portions 3340 are integrally formed with second actuating component 3300. In addition, diagonal portions 3340 can add a curved or sloped interface to the actuating component relative to blade actuating component described earlier (see FIG. 12) in which the intersection between drive shaft portion 320 and blade engaging portion 322 is substantially perpendicular.

Figure 34:
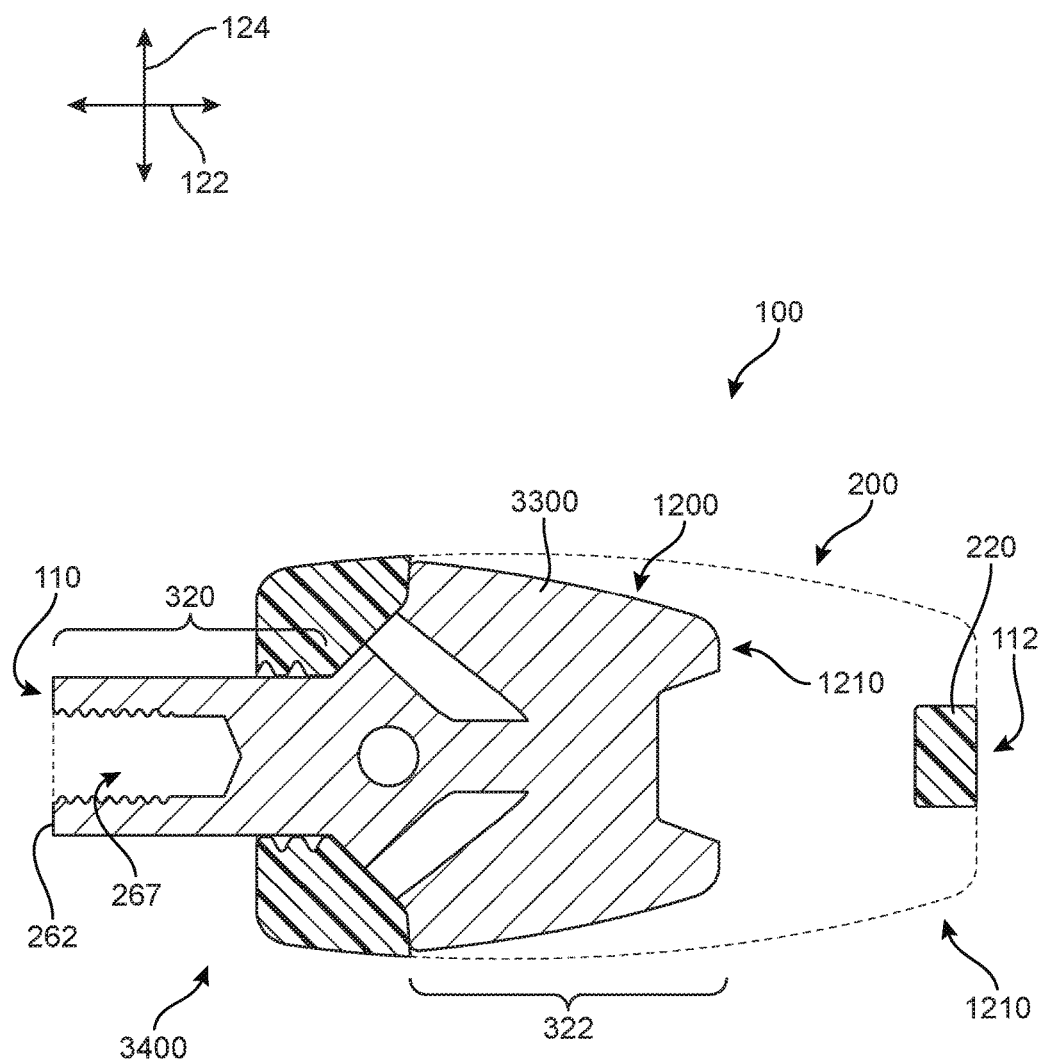
FIG. 34 is a cross-sectional view of an a body and a blade actuating component in the insertion position, according to another embodiment.
Figure 35:
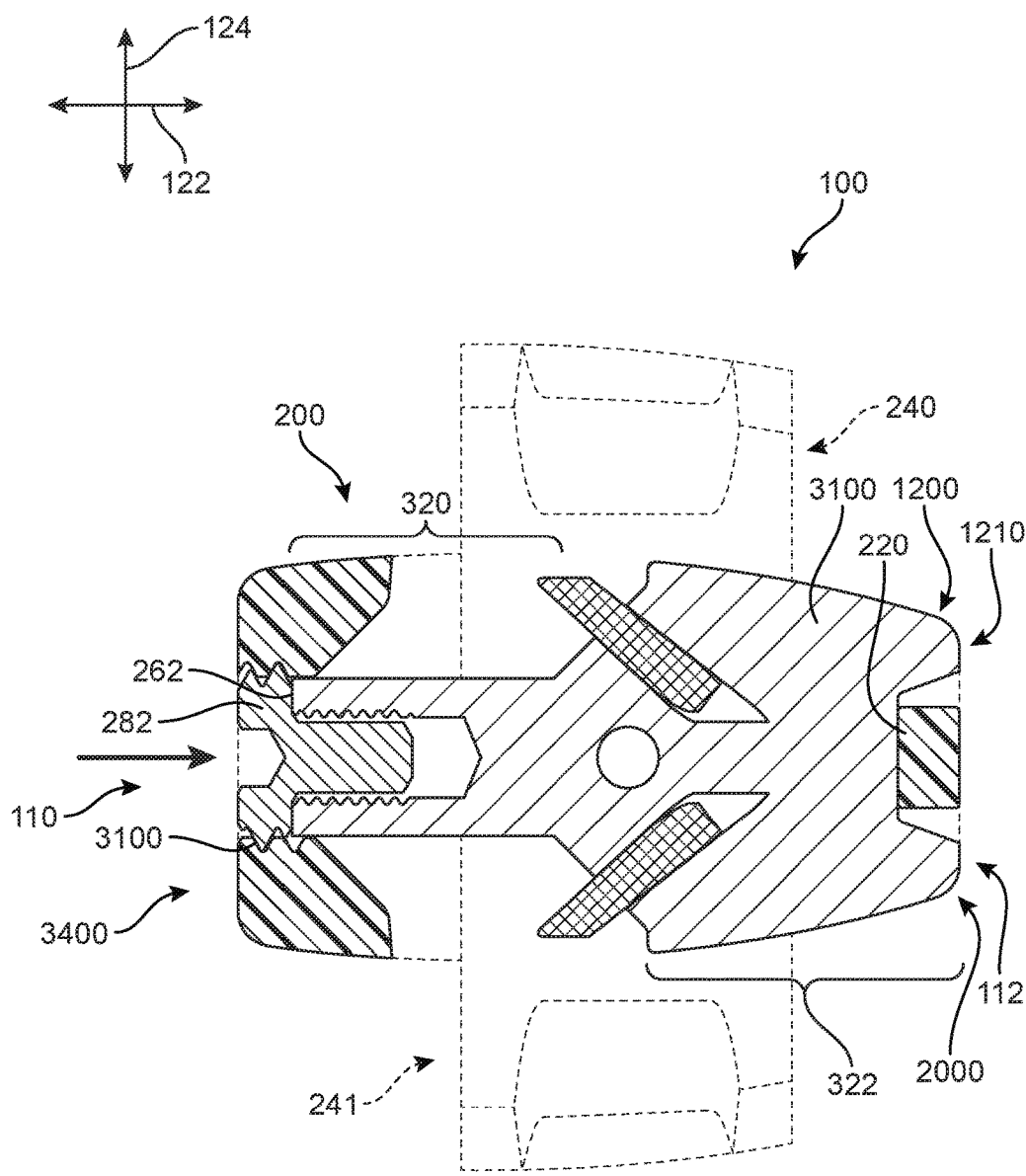
FIG. 35 is a cross-sectional view of an a body and a blade actuating component in the deployed position, according to another embodiment.

In order to provide greater detail with respect to the initial insertion position and the deployed position, FIGS. 34 and 35 provide two cross-sectional views of the implant prior to the application of an impacting force (see FIG. 26) and subsequent to the application of the impacting force. It should be noted that while FIGS. 34 and 35 employ second actuating component 3300, the general operation and transition from insertion to deployment of implant 100 remains substantially the same to the process described above with respect to blade actuating component 260. In FIG. 34, second actuating component 3300 is disposed such that driven end 262 extends distally outward and away from an anterior end 3400 of body 200. The remainder of second actuating component 3300 is positioned such that it is offset relative to the interior space of the implant along posterior-anterior axis 122. In other words, the majority of blade engaging portion 322 is disposed nearer to anterior end 3400 than to posterior end 2000 of body 200 in the insertion position.

However, when an impacting force is applied to driven end 262, the substantial entirety of second actuating component 3300 can be disposed within the internal space of the body. Furthermore, actuating posterior end 1200 can move translationally from the main opening of the central hollow region in body 200 toward the posterior opening. It can be seen that a portion of posterior opening 642 is filled with or bridged by a central portion of cover 220. As actuating posterior end 1200 approaches the posterior opening, receiving portion 1210 comprising the two-pronged mouth shown in FIG. 33 can slide or be positioned above the superior surface and below the inferior surface of cover 220, helping to secure the assembly in place and forming a continuous outer surface.

Furthermore, as noted above, in FIG. 34 it can be seen that threaded opening 267 of driven shaft portion 320 can be configured to receive a threaded driving tool. In addition, as shown in FIG. 35, threaded flanged head 282 of the locking screw engages with grooved portion 3100 formed in the structure of body 200, and the locking screw body is smoothly inserted within the channel provided by threaded opening 267. Driven end 262 can be positioned directly adjacent to the posterior end of grooved portion 3100 when implant 100 is in the deployed position. In other words, once implant 100 is in the deployed position, driven end 262 is disposed such that it is spaced apart from the outer opening formed in body 200 by the region comprising grooved portion 3100.

Insertion Process

As noted above, embodiments of implant 100 can make use of features or structures disclosed in the "Insertion Tool For Implant And Methods of Use" application. In some embodiments, implant 100 can be configured for use with a single tool that can significantly facilitate the implantation process. For example, whether a surgeon approaches the disc space from an anterior approach can be dependent on how comfortable the surgeon is with the anterior approach and operating around the aorta and vena cava. By approaching a patient from the anterior side, there can be a risk of vessel injury, as the aorta and vena cava lie in front of the spine. However, the benefits of added stability and fusion area very often outweigh the risks of the extra surgery, and the process of deployment provided herein can help lower such risks.

Figure 36:
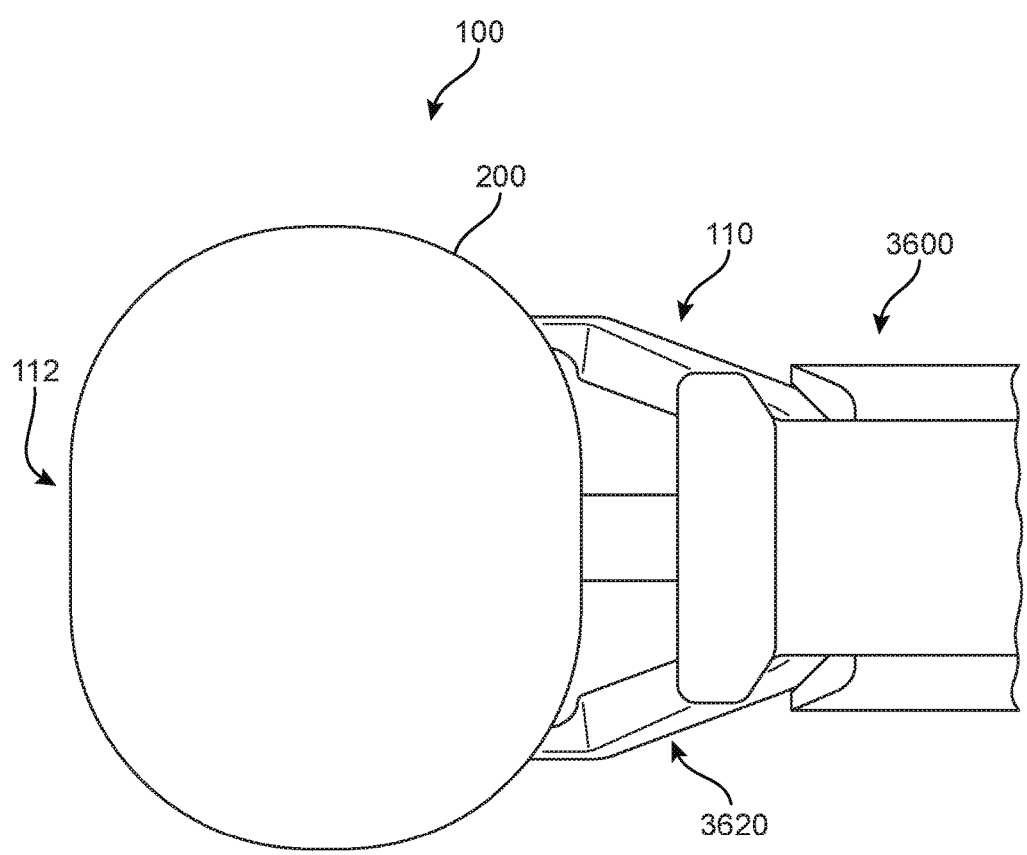
FIG. 36 is a schematic top-down view of an implant and an insertion tool.
Figure 37:
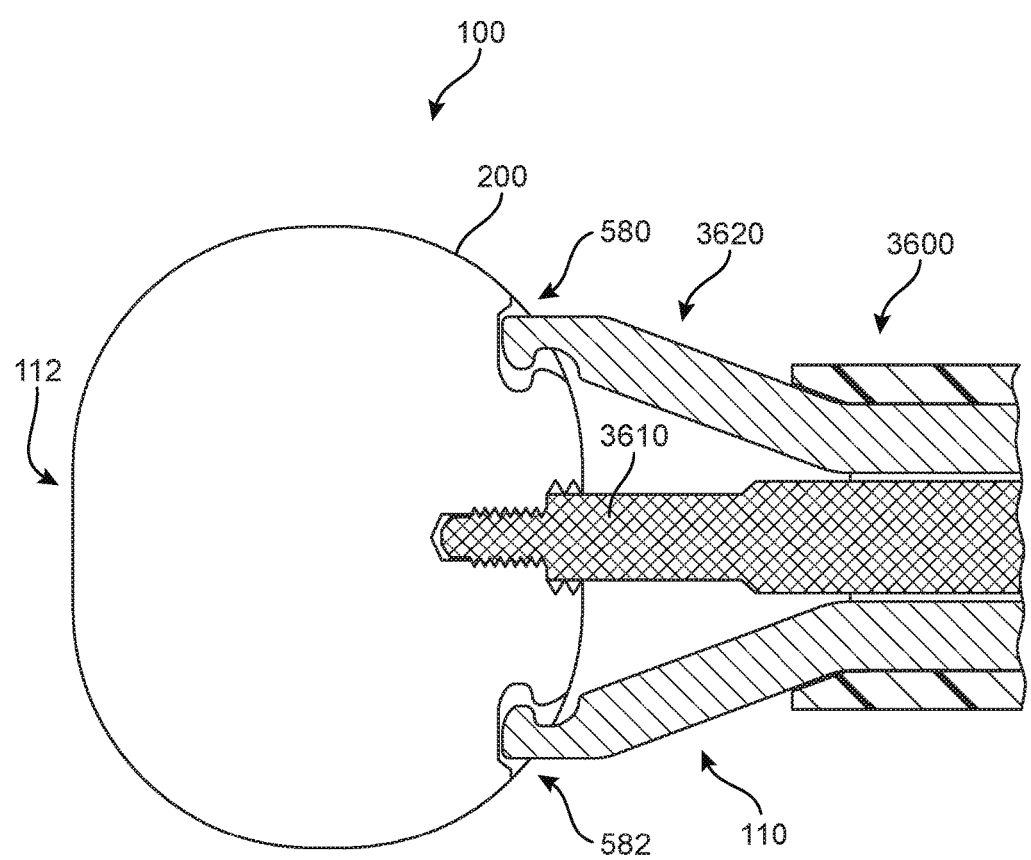
FIG. 37 is a schematic cross-sectional top-down view of the insertion tool with a representation of an implant of FIG. 36.

In some embodiments, body 200 may include attachment points for an insertion instrument. In FIGS. 36 and 37, a portion of an insertion tool 3600 is shown with implant 100. In FIG. 36, insertion tool 3600 is shown as it holds or grasps implant 100. In FIG. 37, the same view of FIG. 36 is shown in a partial cross-section to reveal the engagement of a threaded driver 3610 in guide opening 222.

Body 200 may include provisions for interacting with insertion tool 3600. For example, as seen in FIG. 37, body 200 may include a first cavity 580 and a second cavity 582 (where first cavity 580 refers to first aperture 480 as identified in FIG. 6). Each of first cavity 580 and second cavity 582 may receive the ends of an insertion tool 3600 to improve the grip of the tool on implant 100 during insertion into (or removal from) between the vertebrae of the spine. Furthermore, the same insertion tool 3600 can be utilized to transition implant 100 from the insertion position to the deployed position. As shown in FIGS. 36 and 37, insertion tool 3600 can be used to grasp the implant body. While the implant body is grasped by two gripping jaws 3620, the blade actuating component can be controlled and/or driven by threaded driver 3610. This arrangement can maintain the blades in a retracted position during implant insertion and transfers the impact loads from the surgeon when the threaded cover is removed from the proximal end. Thus, the insertion step, deployment step, and locking screw insertion step can occur through the use of a single tool, and through interaction primarily with only the anterior facing side of the implant. Furthermore, as blade actuating component is pushed inward or outward, there is rotation associated with the threaded driver. The use of insertion tool 3600 and the single guide opening 222 allows the rotation to be generally enclosed or shielded within the jaws of the insertion tool. This process can serve to reduce the risks associated with the insertion of various foreign objects into the patient.

Implant Dimensions

In different embodiments, the size of an implant could vary. In some embodiments, an implant could have any length. Embodiments could have lengths ranging from 40 mm to 60 mm. In some cases, a manufacturer could provide multiple implant options with lengths varying between 40 mm and 60 mm in 5 mm increments. In some embodiments, an implant could have any height. Embodiments could have a height ranging from 4 mm to 16 mm. In some cases, a manufacturer could provide implants with heights varying from 4 mm to 16 mm in 2 mm increments. Embodiments could have widths (i.e., size along the posterior-anterior axis) of 18 mm, 22 mm, 26 mm as well as other sizes.

Embodiments can also be constructed with various lordosis angles, that is, angles of incline between the posterior and anterior sides. Embodiments could be configured with lordosis angles of 8, 15 and 20 degrees, for example. In other embodiments, other lordosis angles could be used for an implant. Furthermore, in some embodiments, the blades can be angled to accommodate additional implants or other implanted device in the spine that are located at adjacent levels, fostering stabilization in the patient's system.

Alignment Features

Embodiments may optionally include one or more alignment features. Exemplary alignment features include, but are not limited to, windows for fluoroscopy positioning, windows for blade deployment validation, windows for aligning a blade actuating component with one or more blades, as well as various other kinds of alignment features. Referring to FIG. 4, body 200 of implant 100 includes a central alignment window (referred to as fourth aperture 486 in FIG. 4). Additionally, as shown in FIG. 13, blade 241 includes an alignment window 297. Alignment window 297 may align with the central alignment window when blade 241 is fully retracted. Moreover, blade actuating component 260 includes an actuating alignment window 277, as shown in FIG. 12. Actuating alignment window 277 may align with the implant body center line when the first blade and the second blade are fully deployed or fully retracted. One or more of these windows (i.e., the central alignment window or actuating alignment window 277) may also facilitate fluoroscopy positioning and may be used to confirm blade deployment. For example, in some cases, when the first blade and the second blade are fully deployed, the blades may clear actuating alignment window 277 of blade actuating component 260.

In some embodiments, the dovetail connections can help to more precisely control the blade position in both directions. Some embodiments of the implant may also include one or more stroke limiting stops. For example, there may be two stroke limiting stops formed on blade actuating component 260. These stops may help prevent over travel of blade actuating component 260. Specifically, a stroke limiting stop may contact the internal surfaces of body 200. In other words, the blade actuating component has a limited stroke dictated by the length of its distal portion and the inside depth of the implant, measured from the inside of the implant proximal wall and the inside surface of the cover that is pinned in place.

Materials

The various components of an implant may be fabricated from biocompatible materials suitable for implantation in a human body, including but not limited to, metals (e.g. titanium, titanium alloy, stainless steel, cobalt-chrome, or other metals), synthetic polymers (e.g. PEEK or PEKK), ceramics, and/or their combinations, depending on the particular application and/or preference of a medical practitioner.

Generally, the implant can be formed from any suitable biocompatible, non-degradable material with sufficient strength. Typical materials include, but are not limited to, titanium, biocompatible titanium alloys (e.g. Titanium Aluminides (including gamma Titanium Alum inides), $Ti_6$—$Al_4$—V ELI (ASTM F 136 and ASTM F 3001), or $Ti_6$—$Al_4$—V (ASTM F 1108, ASTM F 1472, and ASTM F 2989) and inert, biocompatible polymers, such as polyether ether ketone (PEEK) (e.g. PEEK-OPTIMA®, Invibio Inc, Zeniva®, Solvay Inc., or others). Optionally, the implant contains a radiopaque marker to facilitate visualization during imaging when constructed of radiolucent biomaterials.

In different embodiments, processes for making an implant can vary. In some embodiments, the entire implant may be manufactured and assembled via traditional and CNC machining, injection-molding, cast or injection molding, insert-molding, co-extrusion, pultrusion, transfer molding, overmolding, compression molding, 3-Dimensional (3-D) printing, dip-coating, spray-coating, powder-coating, porous-coating, milling from a solid stock material and their combinations.

In one embodiment, body 200 may be produced by Additive Manufacturing. Specifically, Direct Metal Laser Sintering (DMLS) using powder Ti-6Al-4V ELI, and then traditional or CNC machined in specific locations to precise dimensions. Moreover, in one embodiment, as shown in FIG. 5, blade actuating component 260, first blade 241, second blade 242, cover 220, pins 290 and locking screw 280 may also be made of a material including titanium.

Implantation

Some embodiments may use a bone growth promoting material, including bone graft or bone graft substitute material. As used herein, a "bone growth promoting material" (BGPM) is any material that helps bone growth. Bone growth promoting materials may include provisions that are freeze dried onto a surface or adhered to the metal through the use of linker molecules or a binder. Examples of bone growth promoting materials are any materials including bone morphogenetic proteins (BMPs), such as BMP-1, BMP-2, BMP-4, BMP-6, and BMP-7. These are hormones that convert stem cells into bone forming cells. Further examples include recombinant human BMPs (rhBMPs), such as rhBMP-2, rhBMP-4, and rhBMP-7. Still further examples include platelet derived growth factor (PDGF), fibroblast growth factor (FGF), collagen, BMP mimetic peptides, as well as RGD peptides. Generally, combinations of these chemicals may also be used. These chemicals can be applied using a sponge, matrix or gel.

Some bone growth promoting materials may also be applied to an implantable prosthesis through the use of a plasma spray or electrochemical techniques. Examples of these materials include, but are not limited to, hydroxyapatite, beta tri-calcium phosphate, calcium sulfate, calcium carbonate, as well as other chemicals.

A bone growth promoting material can include, or may be used in combination with a bone graft or a bone graft substitute. A variety of materials may serve as bone grafts or bone graft substitutes, including autografts (harvested from the iliac crest of the patient's body), allografts, demineralized bone matrix, and various synthetic materials.

Some embodiments may use autograft. Autograft provides the spinal fusion with calcium collagen scaffolding for the new bone to grow on (osteoconduction). Additionally, autograft contains bone-growing cells, mesenchymal stem cells and osteoblast that regenerate bone. Lastly, autograft contains bone-growing proteins, including bone morphogenic proteins (BMPs), to foster new bone growth in the patient.

Bone graft substitutes may comprise synthetic materials including calcium phosphates or hydroxyapatites, stem cell containing products which combine stem cells with one of the other classes of bone graft substitutes, and growth factor containing matrices such as INFUSE® (rhBMP-2-containing bone graft) from Medtronic, Inc.

It should be understood that the provisions listed here are not meant to be an exhaustive list of possible bone growth promoting materials, bone grafts or bone graft substitutes.

In some embodiments, BGPM may be applied to one or more outer surfaces of an implant. In other embodiments, BGPM may be applied to internal volumes within an implant. In still other embodiments, BGPM may be applied to both external surfaces and internally within an implant.

While various embodiments have been described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with, or substituted for, any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:
1. An implant, comprising: a housing having a first axis;
 a blade having a retracted position in the housing and an extended position where the blade extends outwardly from the housing; and
 a blade actuating component comprising a driven shaft portion and a blade engaging portion;
 wherein the blade actuating component can move the blade between the retracted position and the extended position;
 the housing including a first end including a guide opening, the guide opening comprising a hollow grooved portion and a chamber portion, the hollow grooved portion being connected to the chamber portion;
 the chamber portion of the guide opening having a first cross-sectional shape and a portion of the driven shaft portion of the blade actuating component having a second cross-sectional shape that corresponds to the first cross-sectional shape such that the chamber portion is configured to receive the driven shaft portion and prevent rotation of the driven shaft portion; and
 the hollow grooved portion including a threading configured to receive a threaded fastener configured to prevent a driven end of the bone actuating component from moving from the chamber portion into the hollow grooved portion.
2. The implant according to claim 1, wherein the driven shaft portion includes a driven end that is disposed outside of the housing when the blade is in the retracted position, and wherein the blade transitions from the retracted position to the extended position when a force is applied to the driven end.

3. The implant according to claim 1, wherein the chamber portion has a substantially rectangular cross-sectional shape in a vertical plane, and wherein the driven shaft portion has a substantially rectangular cross-sectional shape in the vertical plane.

4. The implant according to claim 1, wherein the first axis extends between an anterior side to a posterior side of the implant.

5. The implant according to claim 4, wherein the first end is associated with the anterior side of the implant.

6. The implant according to claim 1, wherein the blade actuating component can translate through the housing in directions parallel to the first axis.

7. The implant according to claim 1, further including a threaded fastener configured to prevent the driven end from moving from the chamber portion into the hollow grooved portion.

8. The implant according to claim 7, wherein the threaded fastener includes a flanged head portion joined to a body portion, wherein the flanged head portion includes a threaded segment, wherein the threaded segment corresponds to the threading of the hollow grooved portion.

9. The implant according to claim 8, wherein the hollow grooved portion of the guide opening is larger than the chamber portion of the guide opening.

10. An implant, comprising:
a body having a first axis;
a blade having a retracted position in the body and an extended position where the blade extends outwardly from the body;
the blade also having a distal face and a proximal face;
the blade having a channel-like, C-shaped cross-sectional geometry having a channel defined by a first blade portion, a second blade portion, and a third blade portion, wherein the first blade portion and the third blade portion each extend at an angle from the second blade portion to define the channel between the first blade portion and the second blade portion;
the blade further comprising a bridge portion disposed adjacent to the distal face in the channel and extending between the first blade portion and the third blade portion in order to provide structural reinforcement to the blade;
a blade actuating component that can translate through the body in directions parallel to the first axis; and
wherein the blade actuating component can move the blade between the retracted position and the extended position.

11. The implant according to claim 10, wherein the blade has an anterior edge and a posterior edge, wherein the body includes a first retaining channel and a second retaining channel, wherein the anterior edge of the blade is received in the first retaining channel and wherein the posterior edge of the blade is received in the second retaining channel.

12. The implant according to claim 10, wherein the blade has a first bend where the first blade portion and the second blade portion meet at a nonzero angle.

13. The implant according to claim 10, wherein a posterior side of the body includes a posterior opening extending between a first end portion and a second end portion, and wherein a cover is attached to the body to bridge the posterior opening.

14. The implant according to claim 13, wherein the first end portion includes a first recess configured to receive a portion of the cover.

15. The implant according to claim 14, wherein a posterior end of the blade actuating component includes a receiving portion, and wherein the receiving portion is disposed above a superior surface of the cover and below an inferior surface of the cover when the cover is attached to the body and the blade is in the retracted position.

16. The implant according to claim 10, wherein the blade actuating component includes a channel that extends diagonally on a side of the blade actuating component and is configured to receive a protruding portion of the blade.

17. An implant, comprising:
a housing, a first blade, and a blade actuating component;
the first blade having a retracted position in the housing and an extended position where the first blade extends outwardly from the housing;
the blade actuating component configured to translate through the housing in directions parallel to a first axis, the first axis extending from an anterior side of the implant to a posterior side of the implant; and
the blade actuating component comprising a driven shaft portion and a blade engaging portion, the driven shaft portion being disposed at least partially outside of the housing when the first blade is the retracted position, the driven shaft portion being disposed entirely within the housing when the first blade is in the extended position;
wherein the driven shaft portion includes a threaded opening extending in a direction substantially aligned with the first axis.

18. The implant according to claim 17, wherein the housing includes a guide opening into which the blade actuating component is received, the guide opening having a hollow grooved portion and a chamber portion, the hollow grooved portion including a threading configured to receive a threaded fastener.

19. The implant according to claim 17, wherein the housing includes an anterior opening formed in an anterior side of the housing, wherein the driven shaft portion extends through the anterior opening when the first blade is in the retracted position.

20. The implant according to claim 19, wherein the anterior side of the housing includes at least a first cavity configured to engage with an insertion tool.

21. The implant according to claim 17, further comprising a second blade, the first blade extending distally upward from the housing in the extended position and the second blade extending distally downward from the housing in the extended position.

22. The implant according to claim 21, wherein the first blade has a channel-like geometry and the second blade has a channel-like geometry that is substantially similar to the first blade.

23. The implant according to claim 17, wherein the blade actuating component includes a diagonal portion disposed toward a center of the blade actuating component.

24. The implant according to claim 17, wherein the driven shaft portion includes a driven end that is disposed outside of the housing when the blade is in the retracted position, and wherein the blade transitions from the retracted position to the extended position when a force is applied to the driven end.

25. The implant according to claim 24, wherein an outer edge of the blade is disposed in a central region of the housing in the retracted position, and wherein the outer edge of the blade is positioned centrally relative to the housing in the extended position.

26. A system, comprising:
an implant, including:
a housing, a first blade, and a blade actuating component;
the first blade having a retracted position in the housing and an extended position where the first blade extends outwardly from the housing;
the blade actuating component configured to translate through the housing in directions parallel to a first axis, the first axis extending from an anterior side of the implant to a posterior side of the implant; and
the blade actuating component comprising a driven shaft portion and a blade engaging portion, the driven shaft portion being disposed at least partially outside of the housing when the first blade is the retracted position, the blade actuating component being disposed entirely within the housing when the first blade is in the extended position;
wherein the driven shaft portion includes a threaded opening extending in a direction substantially aligned with the first axis;
an insertion tool configured to grip the housing during insertion of the implant, wherein the insertion tool further comprises a threaded driver configured to engage with the threaded opening to transition the first blade from the retracted position to the extended position; and
a threaded fastener configured to be secured to the implant with the insertion tool to lock the first blade in the extended position.

* * * * *